US009913922B2

United States Patent
Murayama et al.

(10) Patent No.: US 9,913,922 B2
(45) Date of Patent: Mar. 13, 2018

(54) STERILIZING COMPONENT REMOVAL DEVICE, DISINFECTION DEVICE, DISINFECTED ENVIRONMENT MAINTAINING SYSTEM, AND STERILIZING COMPONENT REMOVAL METHOD

(71) Applicants: PANASONIC CORPORATION, Osaka (JP); PANASONIC HEALTHCARE CO., LTD., Ehime (JP)

(72) Inventors: Hiroko Murayama, Osaka (JP); Tatsushi Ohyama, Gifu (JP); Masahiro Iseki, Saitama (JP); Hironobu Sekine, Gumma (JP); Koichi Kobayashi, Tochigi (JP); Hiroshi Yamamoto, Osaka (JP)

(73) Assignees: PANASONIC CORPORATION, Osaka (JP); Panasonic Healthcare Co., Ltd., Ehime (JP)

( * ) Notice: Subject to any disclaimer, the term of this patent is extended or adjusted under 35 U.S.C. 154(b) by 83 days.

(21) Appl. No.: 14/673,834

(22) Filed: Mar. 30, 2015

(65) Prior Publication Data
US 2015/0273097 A1    Oct. 1, 2015

(30) Foreign Application Priority Data

Mar. 31, 2014   (JP) ................. 2014-072151

(51) Int. Cl.
| B08B 3/00 | (2006.01) |
| A61L 2/20 | (2006.01) |
| A61L 2/14 | (2006.01) |

(52) U.S. Cl.
CPC ............. *A61L 2/208* (2013.01); *A61L 2/14* (2013.01); *A61L 2202/122* (2013.01)

(58) Field of Classification Search
CPC .... A61L 2/20; A61L 2/208; A61L 9/00; B01J 19/087; B01J 2219/0894; B01J 2219/0875; B01J 2219/24
USPC ............................ 134/198; 422/129, 186.04
See application file for complete search history.

(56) References Cited

U.S. PATENT DOCUMENTS

| 8,398,932 B2 | 3/2013 | Busujima |
| 2004/0245281 A1* | 12/2004 | Oke .................. A61L 2/16 222/1 |
| 2009/0227008 A1 | 9/2009 | Busujima |
| 2010/0170867 A1 | 7/2010 | Hayakawa |
| 2012/0275965 A1 | 11/2012 | Yokoi et al. |

(Continued)

FOREIGN PATENT DOCUMENTS

| JP | 2004-357888 A | 12/2004 |
| JP | 2006-087343 A | 4/2006 |

(Continued)

OTHER PUBLICATIONS

Japanese Office Action dated Oct. 24, 2017 issued in Japanese Patent Application No. 2014-072151 (with English translation).

*Primary Examiner* — Eric W Golightly
(74) *Attorney, Agent, or Firm* — McDermott Will & Emery LLP

(57) ABSTRACT

A sterilizing component removal device which reduces a sterilizing component sprayed in a working chamber having an outlet includes a sprayer which supplies, in an atomized manner, a liquid different from the sterilizing component into the working chamber.

11 Claims, 18 Drawing Sheets

(56) References Cited

U.S. PATENT DOCUMENTS

2012/0275967 A1 11/2012 Yokoi et al.
2013/0336844 A1 12/2013 Yokoi et al.
2015/0017063 A1 1/2015 Yokoi et al.

FOREIGN PATENT DOCUMENTS

| JP | 2007-259715 A | 10/2007 |
| JP | 2012-231917 A | 11/2012 |
| JP | 2012-231918 A | 11/2012 |
| JP | 2013-209164 A | 10/2013 |

* cited by examiner

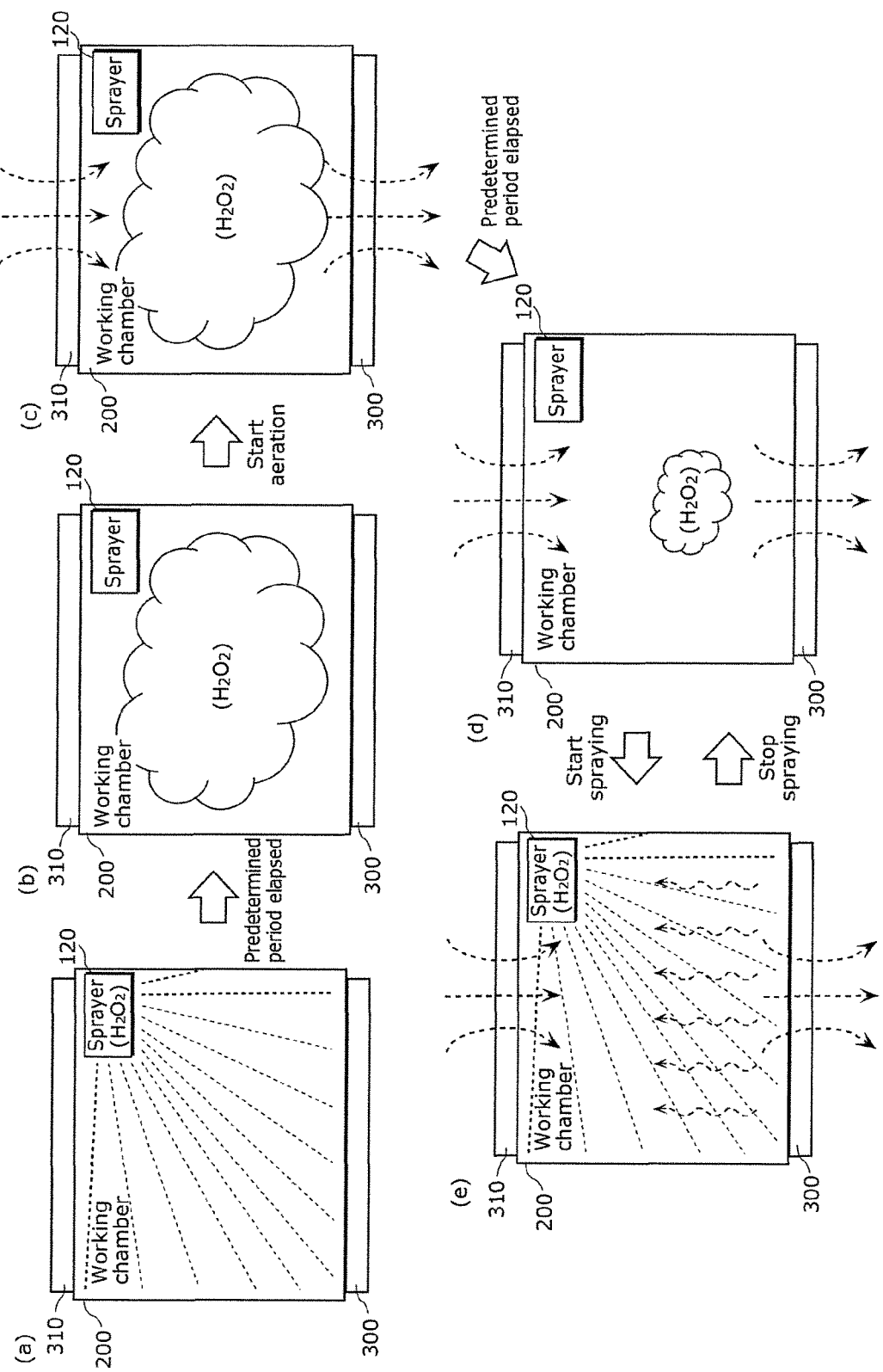

STERILIZING COMPONENT REMOVAL DEVICE, DISINFECTION DEVICE, DISINFECTED ENVIRONMENT MAINTAINING SYSTEM, AND STERILIZING COMPONENT REMOVAL METHOD

CROSS REFERENCE TO RELATED APPLICATION

The present application is based on and claims priority of Japanese Patent Application No. 2014-072151 filed on Mar. 31, 2014. The entire disclosure of the above-identified application, including the specification, drawings and claims is incorporated herein by reference in its entirety.

FIELD

The present disclosure relates to a sterilizing component removal device, a disinfection device, a disinfected environment maintaining system, a sterilizing component removal method, and so on.

BACKGROUND

Conventionally, cells, microorganisms, and others are cultured in culture chambers such as glove boxes, for example. A culture chamber needs to be always kept clean, and thus needs to be sterilized before a cell, for instance, is cultured therein.

For example, Patent Literature 1 discloses a culture device which sterilizes the inside of a culture chamber. The culture device disclosed in Patent Literature 1 includes a sterilizing gas generator which supplies sterilizing gas into the culture chamber, and an ultraviolet generator which emits ultraviolet rays. The culture device disclosed in Patent Literature 1 supplies sterilizing gas into the culture chamber, and thereafter decomposes the sterilizing gas by emitting ultraviolet rays, thus reducing a concentration of the sterilizing gas. In this manner, a sterilization period can be shortened.

CITATION LIST

Patent Literature

[PTL 1] Japanese Unexamined Patent Application Publication No. 2007-259715

SUMMARY

Technical Problem

The above conventional culture device, however, has difficulty in decomposing liquefied sterilizing gas which remains in a place where ultraviolet rays do not reach. Accordingly, the remaining sterilizing gas causes problems, such as extension of a sterilization period and harmful effects on cultures such as cells and microorganisms.

In view of this, the present disclosure provides a sterilizing component removal device, a disinfection device, a disinfected environment maintaining system, and a sterilizing component removal method which allow removal of a sterilizing component in a shorter time.

Solution to Problem

In order to address the above problems, a sterilizing component removal device according to an aspect of the present disclosure is a sterilizing component removal device which removes a sterilizing component sprayed in a working chamber having an outlet, the sterilizing component removal device including a first sprayer which supplies, in an atomized manner, a liquid different from the sterilizing component into the working chamber.

Advantageous Effects

According to the present disclosure, a sterilizing component can be removed in a shorter time.

BRIEF DESCRIPTION OF DRAWINGS

These and other objects, advantages and features of the disclosure will become apparent from the following description thereof taken in conjunction with the accompanying drawings that illustrate a specific embodiment of the present disclosure.

FIG. 6C illustrates internal states of the working chamber in process steps, which is included in the disinfected environment maintaining system according to Embodiment 1.

Figure 1:
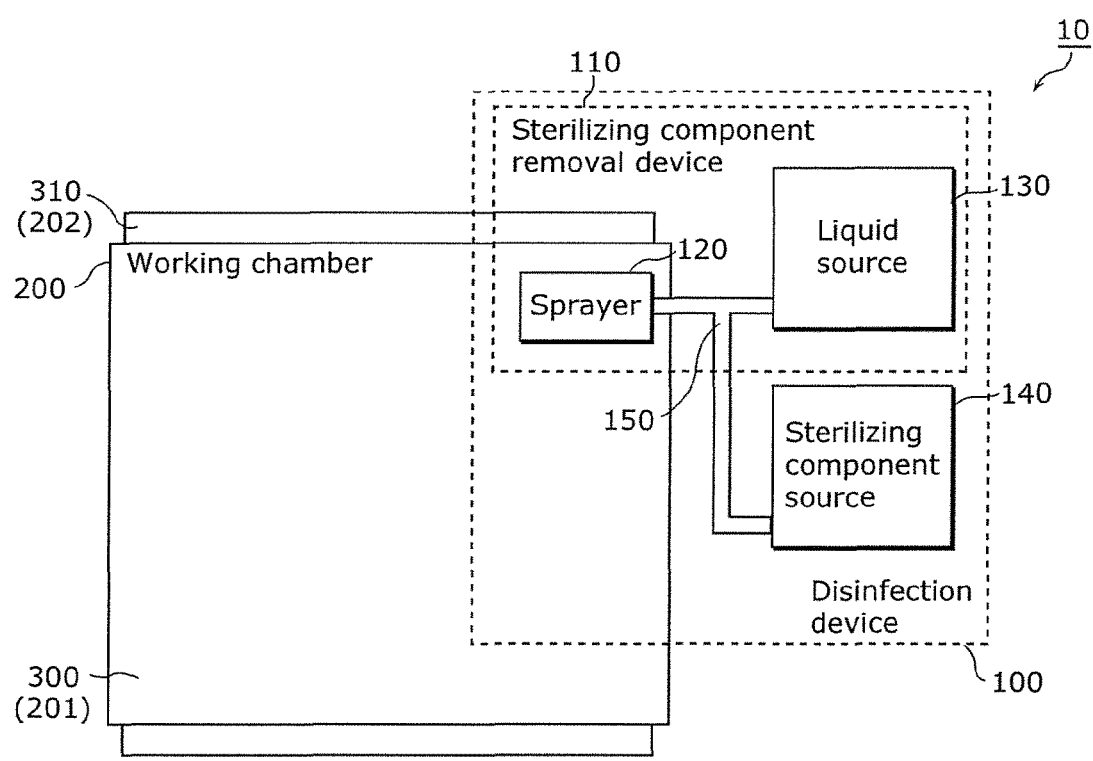
FIG. 1 is a configuration diagram illustrating a disinfected environment maintaining system according to Embodiment 1.

DESCRIPTION OF EMBODIMENTS (Summary of Present Disclosure)

In order to address the above problems, a sterilizing component removal device according to an aspect of the present disclosure is a sterilizing component removal device which removes a sterilizing component sprayed in a working chamber having an outlet, the sterilizing component removal device including a first sprayer which supplies, in an atomized manner, a liquid different from the sterilizing component into the working chamber.

In this manner, gasification of the sterilizing component can be promoted by the liquid supplied in the atomized manner, and the gasified sterilizing component can be expelled through the outlet. Accordingly, the sterilizing component can be removed in a shorter time. It should be noted that in this specification, "remove" includes not only completely eliminating the sterilizing component, but also sufficiently reducing the sterilizing component. In other words, "remove" means making the sterilizing component "harmless". For example, "remove" and "(making) harmless" include reducing the sterilizing component to such an extent that a cell to be cultured and a microorganism (culture) are not affected.

For example, the first sprayer may supply, in the atomized manner, the liquid which includes a substance which promotes gasification of the sterilizing component which is liquefied, into the working chamber.

Accordingly, the liquid includes the substance which promotes gasification, thus further reducing a time for removing the sterilizing component.

For example, the first sprayer may supply, in the atomized manner, the liquid which includes an active species which decomposes the sterilizing component, into the working chamber.

Accordingly, not only gasification of the sterilizing component is promoted, but also the sterilizing component is decomposed by the active species, thus further reducing a time for removing the sterilizing component.

For example, the sterilizing component removal device may further include: a liquid source for supplying the liquid to the first sprayer; and a plasma generator which generates plasma to generate the active species in the liquid stored in the liquid source.

Accordingly, the active species is efficiently generated by plasma, thus further reducing a time for removing the sterilizing component.

A disinfection device according to an aspect of the present disclosure includes the sterilizing component removal device, wherein the first sprayer further supplies, in the atomized manner, the sterilizing component into the working chamber.

Accordingly, the sterilizing component and the liquid are sprayed using a single sprayer, and thus can be sprayed at the same area. Consequently, a probability that the sterilizing component and the liquid come into contact can be increased, thus further promoting gasification and reducing a time for removing the sterilizing component.

For example, a disinfection device may include: the sterilizing component removal device; and a second sprayer which supplies, in an atomized manner, the sterilizing component into the working chamber.

This prevents the sterilizing component and the liquid from coming into contact before being sprayed, and thus the gasification promoting effect by the liquid can be further increased. Accordingly, a time for removing the sterilizing component can be further reduced.

A disinfected environment maintaining system according to an aspect of present disclosure includes: the sterilizing component removal device or the disinfection device; the working chamber; and an expulsion device which expels gas from the working chamber through the outlet.

Accordingly, gas, or specifically, the gasified sterilizing component can be efficiently expelled from the working chamber. Thus, a time for removing the sterilizing component can be reduced.

For example, the disinfected environment maintaining system may further include a supply device which supplies gas into the working chamber.

Accordingly, a gas flow can be generated in the working chamber, and the gas can be expelled more efficiently from the working chamber.

A sterilizing component removal method according to an aspect of the present disclosure is a sterilizing component removal method for removing a sterilizing component sprayed in a working chamber having an outlet, the sterilizing component removal method including supplying, in an atomized manner, a liquid different from the sterilizing component into the working chamber.

In this manner, gasification of the sterilizing component is promoted by the liquid supplied in the atomized manner, and the gasified sterilizing component can be expelled through the outlet. Accordingly, the sterilizing component can be removed in a shorter time.

For example, the liquid may be supplied into the working chamber in the atomized manner, while gas is being expelled from the working chamber through the outlet.

This simultaneously causes expulsion of the gas and spraying the liquid (or in other words, promotion of gasification of the sterilizing component), and thus a time for removing the sterilizing component can be further reduced.

For example, the sterilizing component removal method may further include expelling, before supplying the liquid in the atomized manner, gas from the working chamber through the outlet without supplying the liquid into the working chamber in the atomized manner.

Accordingly, the gasified sterilizing component filling the working chamber can be expelled previously, and thus gasification of the sterilizing component can be more effectively promoted by later spraying. Thus, a time for removing the sterilizing component can be reduced.

For example, expelling the gas and supplying the liquid in the atomized manner may be repeated.

In this manner, the liquid is sprayed intermittently while expelling gas, thus promoting gasification of the sterilizing component and expelling the gas effectively. Accordingly, a time for removing the sterilizing component can be reduced.

For example, the liquid may be supplied into the working chamber in the atomized manner in a state where a gas flow in the working chamber is same as a gas flow created when the sterilizing component is supplied into the working chamber.

In this manner, gas flows created when the sterilizing component is sprayed and when the liquid is sprayed are made the same, thus allowing the sterilizing component and the liquid to be sprayed at substantially the same area. Accordingly, a probability that the sterilizing component and the liquid come into contact can be increased, thus further promoting gasification and reducing a time for removing the sterilizing component.

The following specifically describes non-limiting and exemplary embodiments, with reference to the drawings.

The embodiments described below each show a general or specific example. The numerical values, shapes, materials, constituent elements, the arrangement and connection of the constituent elements, steps, the processing order of the steps, and the like described in the following exemplary embodiments are mere examples, and thus are not intended to limit the present disclosure. Further, among the constituent elements in the following embodiments, constituent elements not recited in any of the independent claims defining the most generic part of the inventive concept are described as arbitrary constituent elements.

Embodiment 1

[1. Overview of Disinfected Environment Maintaining System]

Figure 2:
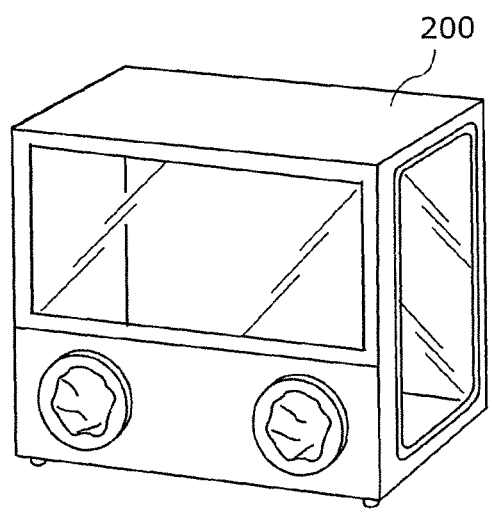
FIG. 2 is an external view illustrating an example of a working chamber in the disinfected environment maintaining system according to Embodiment 1.

The first describes a disinfected environment maintaining system according to Embodiment 1, with reference to FIGS. 1 and 2. FIG. 1 is a configuration diagram illustrating a disinfected environment maintaining system 10 according to the present exemplary embodiment. FIG. 2 is an external view illustrating an example of a working chamber in the disinfected environment maintaining system 10 according to Embodiment 1.

The disinfected environment maintaining system 10 according to the present exemplary embodiment includes a disinfection device which supplies a sterilizing component to the working chamber to disinfect the working chamber, and removes the sterilizing component used for the disinfection. Specifically, in the disinfected environment maintaining system 10, a liquid is sprayed inside the disinfected working chamber to promote gasification of the liquefied sterilizing component. This allows the sterilizing component to be removed in a shorter time.

As illustrated in FIG. 1, the disinfected environment maintaining system 10 includes a disinfection device 100, a working chamber 200, an expulsion device 300, and a supply device 310.

[1-1. Working Chamber]

The working chamber 200 is a housing which has an outlet 201 and an inlet 202. For example, the working chamber 200 is a culture chamber for growing cultures such as a cell and a microorganism. Specifically, the working chamber 200 is a glove box as illustrated in FIG. 2, and is a container having a design which allows only hands to be put inside so that a work can be done in a condition where the open air is blocked. For example, the internal pressure of the working chamber 200 is maintained slightly higher than the atmospheric pressure.

The outlet 201 is an opening for expelling gas from the working chamber 200 to the outside. The outlet 201 can be opened and closed, for example, in conjunction with the operation of the expulsion device 300. The outlet 201 is provided in a lower part of the working chamber 200, for example.

The inlet 202 is an opening for introducing gas from the outside into the working chamber 200. The inlet 202 can be opened and closed in conjunction with the operation of the supply device 310, for example. The inlet 202 is provided in an upper part of the working chamber 200, for example.

It should be noted that the positions where the outlet 201 and the inlet 202 are provided are not limited to the above examples. For example, the outlet 201 and the inlet 202 may be provided in any of the upper, lateral, and bottom surfaces of the working chamber 200. In addition, the working chamber 200 may have plural outlets 201 or inlets 202, or plural outlets 201 and inlets 202. In addition, the outlet 201 and the inlet 202 may each have a filter, for instance, which absorbs moisture in gas.

[1-2. Expulsion Device]

The expulsion device 300 expels gas from working chamber 200 through the outlet 201. Specifically, the expulsion device 300 expels gas which includes a gasified sterilizing component and others from the working chamber 200 to the outside of the working chamber 200 through the outlet 201. For example, the expulsion device 300 is a blower which blows air, such as a fan.

[1-3. Supply Device]

The supply device 310 is a device which supplies gas into the working chamber 200 through the inlet 202. Specifically, the supply device 310 supplies air outside the working chamber 200 into the working chamber 200 through the inlet 202. For example, the supply device 310 is a blower which blows air, such as a fan.

The supply device 310 can produce a flow of gas inside the working chamber 200, together with the expulsion device 300. In this manner, the sterilizing component gasified in the working chamber 200 is expelled to the outside of the working chamber 200 through the outlet 201, along the gas flow. The above-described process of expelling gas from the working chamber 200 by producing a gas flow may be referred to as "aeration" below.

[2. Disinfection Device]

The disinfection device 100 disinfects the inside of the working chamber 200 using a sterilizing component, and removes the sterilizing component used for the disinfection. As illustrated in FIG. 1, the disinfection device 100 includes a sterilizing component removal device 110 and a sterilizing component source 140.

[2-1. Sterilizing Component Removal Device]

The sterilizing component removal device 110 removes a sterilizing component sprayed in the working chamber 200. The sterilizing component removal device 110 includes a sprayer 120, a liquid source 130, and a piping part 150.

[2-1-1. Sprayer]

The sprayer 120 is an example of a first sprayer which supplies, into the working chamber 200, an atomized liquid different from a sterilizing component. For example, the sprayer 120 includes a spray nozzle, and sprays (mists) a liquid which is atomized into a small size of about several to tens of microns, in the working chamber 200.

Specifically, a liquid stored in the liquid source 130 is supplied to the sprayer 120 through the piping part 150. Then, the sprayer 120 atomizes the supplied liquid and sprays the atomized liquid in the working chamber 200. For example, the sprayer 120 sprays atomized pure water in the working chamber 200.

In addition, the sprayer 120 further supplies an atomized sterilizing component into the working chamber 200. Specifically, a liquid sterilizing component stored in the sterilizing component source 140 is supplied to the sprayer 120 through the piping part 150. Then, the sprayer 120 atomizes the supplied liquid sterilizing component, and sprays the atomized sterilizing component in the working chamber 200.

[2-1-2. Liquid Source]

The liquid source 130 supplies a liquid to the sprayer 120. The liquid source 130 is a box-shaped object such as a tank for storing a liquid, for example. As illustrated in FIG. 1, the liquid source 130 is disposed outside the working chamber 200. It should be noted that the liquid source 130 may be disposed inside the working chamber 200. The liquid source 130 and the sprayer 120 are connected by the piping part 150.

The liquid promotes gasification of the sterilizing component. Specifically, if the liquid comes into contact with the sterilizing component, the evaporating temperature of the sterilizing component decreases and gasification of the sterilizing component is promoted, for example. An example of the liquid may be a substance which forms an azeotrope with the sterilizing component by being mixed therewith.

A liquid is water (pure water, $H_2O$), for example. It should be noted that the liquid may be running water or water which already includes a predetermined compound, rather than pure water. For example, the liquid may also include a substance which promotes gasification of a liquefied sterilizing component. A gasification promoting substance is a nitric acid, for example. For example, the gasification promoting substance can dissolve a target sterilizing component and furthermore, lower the boiling point. Such a substance may be alcohol, specifically.

The liquid source 130 includes a liquid-sending device such as a pump for sending a liquid to the piping part 150, for example. Accordingly, the liquid source 130 can supply a liquid to the sprayer 120 through the piping part 150.

[2-1-3. Piping Part]

The piping part 150 is formed using a tubular member such as a pipe, a tube, or a hose, for example. In addition, the piping part 150 has three branches which are connected to the sprayer 120, the liquid source 130, and the sterilizing component source 140. Specifically, the piping part 150 forms a path for supplying, to the sprayer 120, a liquid stored in the liquid source 130, and a sterilizing component stored in the sterilizing component source 140.

It should be noted that a valve, for example, is provided between the liquid source 130 and the branch of the piping part 150, in order to prevent the sterilizing component supplied from the sterilizing component source 140 from being mixed into the liquid in the liquid source 130. Similarly, a valve, for example, is also provided between the sterilizing component source 140 and the branch of the piping part 150, in order to prevent the liquid supplied from the liquid source 130 from being mixed into the sterilizing component in the sterilizing component source 140.

[2-2. Sterilizing Component Source]

The sterilizing component source 140 supplies a sterilizing component to the sprayer 120. The sterilizing component source 140 is a box-shaped object such as a tank for storing a sterilizing component, for example. As illustrated in FIG. 1, the sterilizing component source 140 is disposed outside the working chamber 200. It should be noted that the sterilizing component source 140 may be disposed inside the working chamber 200. The sterilizing component source 140 and the sprayer 120 are connected by the piping part 150.

An example of the sterilizing component is a hydrogen peroxide solution ($H_2O_2$). The sterilizing component is a liquid or gas which includes a component for disinfecting the inside of the working chamber 200. For example, the sterilizing component may be chlorine ($Cl_2$) or the like. Alternatively, the sterilizing component may be ethylene oxide, formalin, glutaraldehyde, peracetic acid, or the like.

The sterilizing component source 140 includes a liquid-sending device such as a pump for sending the sterilizing component to the piping part 150, for example. Accordingly, the sterilizing component source 140 can supply the sterilizing component to the sprayer 120 through the piping part 150.

[3. Time Period for Liquid to Volatilize]

Figure 3:
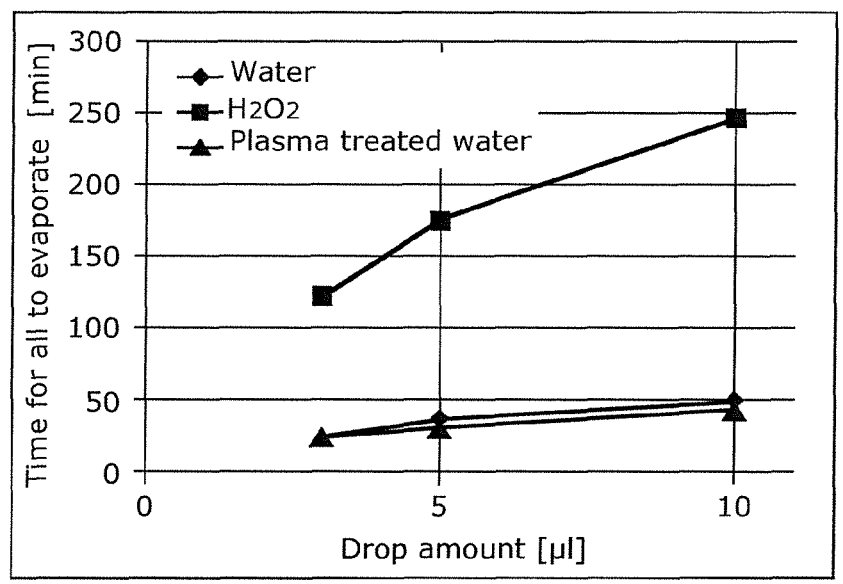
FIG. 3 illustrates results of comparing time periods for water and hydrogen peroxide to volatilize according to Embodiment 1.

The following describes time periods for a liquid and a sterilizing component according to the present exemplary embodiment to volatilize, with reference to FIG. 3. FIG. 3 illustrates comparison results of time periods for water and a hydrogen peroxide solution to volatilize according to the present exemplary embodiment.

Here, one drop (3 μl, 5 μl, 10 μl) of water and one drop of a hydrogen peroxide solution (35%) are put on a glass substrate, and left at room temperature. Then, time periods until the drops evaporate are measured. It should be noted that FIG. 3 also illustrates later-described plasma treated water for comparison.

As is clear from FIG. 3, a hydrogen peroxide solution needs, to evaporate, a time period about 5 times as much as water and plasma treated water. It should be noted that Embodiment 2 describes in detail an example of using plasma treated water.

[4. Operation]

Figure 4:
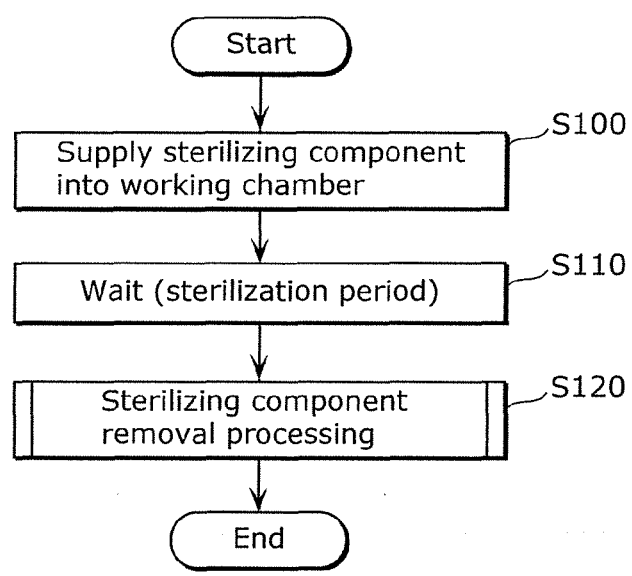
FIG. 4 is a flowchart showing an example of operation of the disinfected environment maintaining system according to Embodiment 1.

The following describes operation of the disinfected environment maintaining system 10 according to the present exemplary embodiment, with reference to FIGS. 4 to 6D. The first describes the overall operation of the disinfected environment maintaining system 10, with reference to FIG. 4. FIG. 4 is a flowchart showing an example of operation of the disinfected environment maintaining system 10 according to the present exemplary embodiment.

First, as shown in FIG. 4, the sprayer 120 supplies a sterilizing component into the working chamber 200 (S100). Specifically, the sterilizing component source 140 supplies, to the sprayer 120, the sterilizing component for a certain period or a certain amount of the sterilizing component. The sprayer 120 sprays the supplied sterilizing component in the working chamber 200.

After supplying the sterilizing component into the working chamber 200, the disinfected environment maintaining system 10 waits a predetermined period (sterilization period) (S110). Specifically, the disinfected environment maintaining system 10 waits a sufficient period for the sterilizing component supplied into the working chamber 200 to disinfect the inside of the working chamber 200. For example, the sterilization period lasts 15 minutes. It should be noted that the sterilizing component sprayed in the working chamber 200 partially gasifies and collects in the working chamber 200.

After the sterilization period has elapsed, the sterilizing component removal device 110 removes the sterilizing component (S120). Specifically, the sterilizing component removal device 110 sufficiently reduces the sterilizing component in the working chamber 200, to an extent that a culture is not affected.

Methods for removing the sterilizing component include four modes, namely, first to fourth modes, as described in the following. The following describes the four modes one by one with reference to FIG. 4 and also FIGS. 5A to 6D.

[4-1. First Mode (Expulsion, then Spraying and Expulsion)]

The first describes a first mode of the sterilizing component removal method according to the present exemplary embodiment, with reference to FIGS. 5A and 6A. In the first mode, gas is expelled first, and thereafter an atomized liquid is supplied while gas is being expelled (thus, gasification of a sterilizing component is promoted).

FIG. 5A is a flowchart showing the first mode of the sterilizing component removal method according to the present exemplary embodiment. FIG. 6A illustrates internal states of the working chamber 200 in process steps in the first mode.

As illustrated in (a) of FIG. 6A, the sprayer 120 supplies a sterilizing component ($H_2O_2$) into the working chamber 200 (S100 in FIG. 4). While the disinfected environment maintaining system 10 waits (leaves the working chamber 200 as it is) for the predetermined sterilization period (S110), the sprayed sterilizing component gasifies inside the working chamber 200 and fills the working chamber 200 as illustrated in (b) of FIG. 6A. The sterilization period lasts 10 to 15 minutes, for example. In this manner, the sterilizing component spreads inside the working chamber 200, thus appropriately disinfecting the working chamber 200.

After the sterilization period has elapsed, the disinfected environment maintaining system 10 removes the sterilizing component used for the disinfection (S120).

As illustrated in FIG. 5A, first, gas supply and gas expulsion (or in other words, aeration) start (S121). Specifically, the supply device 310 supplies gas into the working chamber 200, and simultaneously the expulsion device 300 expels gas from the working chamber 200. Accordingly, the sterilizing component gasified inside the working chamber 200 is expelled outside, as illustrated in (c) of FIG. 6A.

This operation is continued for a predetermined expulsion period (S122), and consequently, the sterilizing component in the working chamber 200 is reduced as illustrated in (d) of FIG. 6A. The expulsion period lasts 5 to 10 minutes, for example. It should be noted that the sterilizing component which has not been gasified yet, or in other words, the liquefied sterilizing component remains in the working chamber 200.

Next, as illustrated in (e) of FIG. 6A, the sprayer 120 starts spraying an atomized liquid (S123). At this time, aeration is being performed. Then, this operation is continued for a predetermined spraying period (S124). Specifically, the atomized liquid is sprayed, or in other words, gasification of the sterilizing component is promoted simultaneously with the expulsion of gas. The spraying period lasts 3 minutes, for example. The amount of the liquid sprayed is 5 ml, for example. This promotes gasification of the sterilizing component still in liquid form, and the sterilizing component is gasified inside the working chamber 200.

Lastly, supply of the atomized liquid and aeration are stopped (S125). Specifically, the sprayer 120 stops spraying the liquid, the supply device 310 stops supplying the gas into the working chamber 200, and the expulsion device 300 stops expelling the gas from the working chamber 200. It should be noted that the expulsion device 300 and the supply device 310 may stop aeration when a predetermined period (for example, 10 minutes) elapses after the sprayer 120 stops spraying the liquid.

It should be noted that in the first mode, a stop of gas supply and gas expulsion, or in other words, a stop of aeration does not necessarily mean a complete stop of a gas flow. Actually, gas is slightly supplied and gas is slightly expelled, thus circulating air between the inside and outside of the working chamber 200. It should be noted that the same also applies to the other modes described below.

It should be noted that, for example, a culture is grown while the aeration is stopped, or in other words, air slightly circulates. Specifically, the state where aeration is stopped and the sterilizing component and the liquid are not sprayed is a normal mode (growing mode) in the disinfected environment maintaining system 10.

As described above, the first mode includes a gas expulsion step of expelling gas from the working chamber 200 through the outlet 201 without supplying an atomized liquid into the working chamber 200, or in other words, the expulsion period (S122), prior to a liquid supply step, that is, the spraying period (S124).

This achieves a reduction in time for removing the sterilizing component, since the sprayer 120 sprays the atomized liquid to promote gasification of the sterilizing component while gas is being expelled from the working chamber 200. In addition, the sterilizing component filling the working chamber 200 is expelled first, thus allowing the liquefied sterilizing component to be gasified effectively.

[4-2. Second Mode (Spraying and Expulsion)]

The following describes a second mode of the sterilizing component removal method according to the present exemplary embodiment, with reference to FIGS. 5B and 6B. In the second mode, gas is expelled simultaneously with the supply of an atomized liquid, from the beginning.

FIG. 5B is a flowchart showing the second mode of the sterilizing component removal method according to the present exemplary embodiment. FIG. 6B illustrates internal states of the working chamber 200 in process steps in the second mode. It should be noted that the processing until the sterilization period elapses is the same as that in the first mode, and thus a description thereof is omitted (see FIG. 4 and (a) and (b) of FIG. 6B).

As shown in FIG. 5B, first, supply of an atomized liquid and gas and gas expulsion are started (S221). Specifically, as illustrated in (c) of FIG. 6B, the supply device 310 supplies gas into the working chamber 200, and also the expulsion device 300 expels gas from the working chamber 200, and furthermore the sprayer 120 supplies an atomized liquid into the working chamber 200. Specifically, the aeration inside the working chamber 200 is started, and simultaneously, the sprayer 120 starts supplying the atomized liquid, or in other words, promotion of gasification of the sterilizing component is started.

Then, this operation is continued for the predetermined spraying period (S124). Specifically, the atomized liquid is sprayed, or in other words, gasification of the sterilizing component is promoted, simultaneously with the expulsion of the gas.

Lastly, supply of the atomized liquid and aeration are stopped (S125). Specifically, the sprayer 120 stops spraying the liquid, the supply device 310 stops supplying gas into the working chamber 200, and the expulsion device 300 stops expelling gas from the working chamber 200. It should be noted that aeration may be stopped after the elapse of a certain time after spraying the liquid is stopped.

As described above, in the second mode, the atomized liquid is supplied into the working chamber 200 while gas is being expelled from the working chamber 200 through the outlet 201 in the liquid supply step, namely, during the spraying period (S124).

This achieves a reduction in time for removing the sterilizing component, since the sprayer 120 sprays the atomized liquid to promote gasification of the sterilizing component while gas is being expelled from the working chamber 200.

[4-3. Third Mode (Intermittent Spraying)]

Figure 5A:
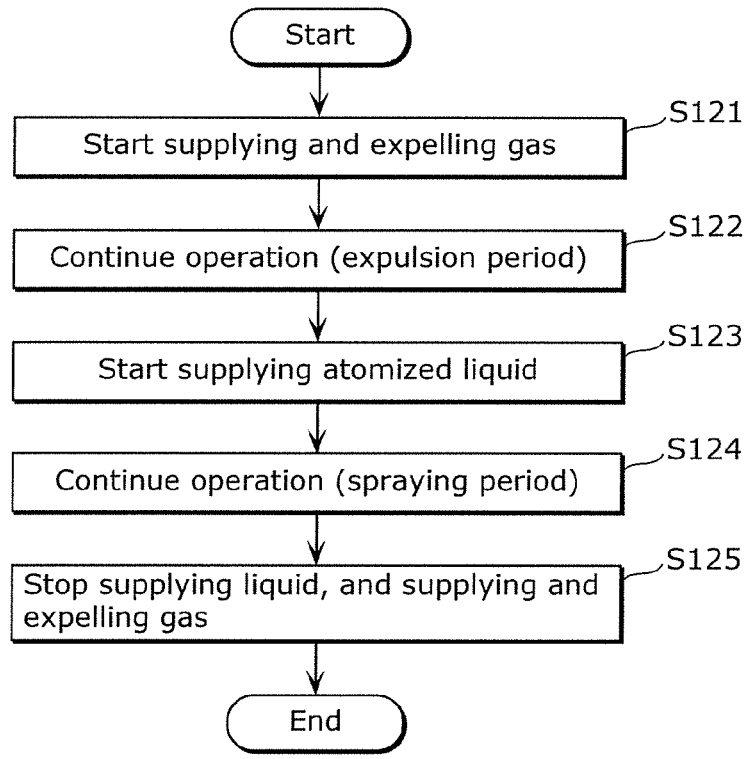
FIG. 5A is a flowchart showing an example of a sterilizing component removal method according to Embodiment 1.
Figure 5B:
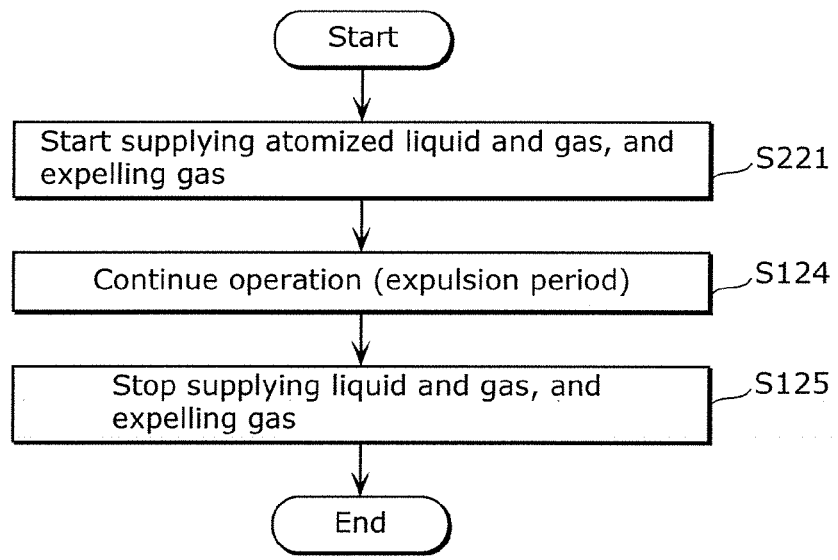
FIG. 5B is a flowchart showing another example of the sterilizing component removal method according to Embodiment 1.
Figure 5C:
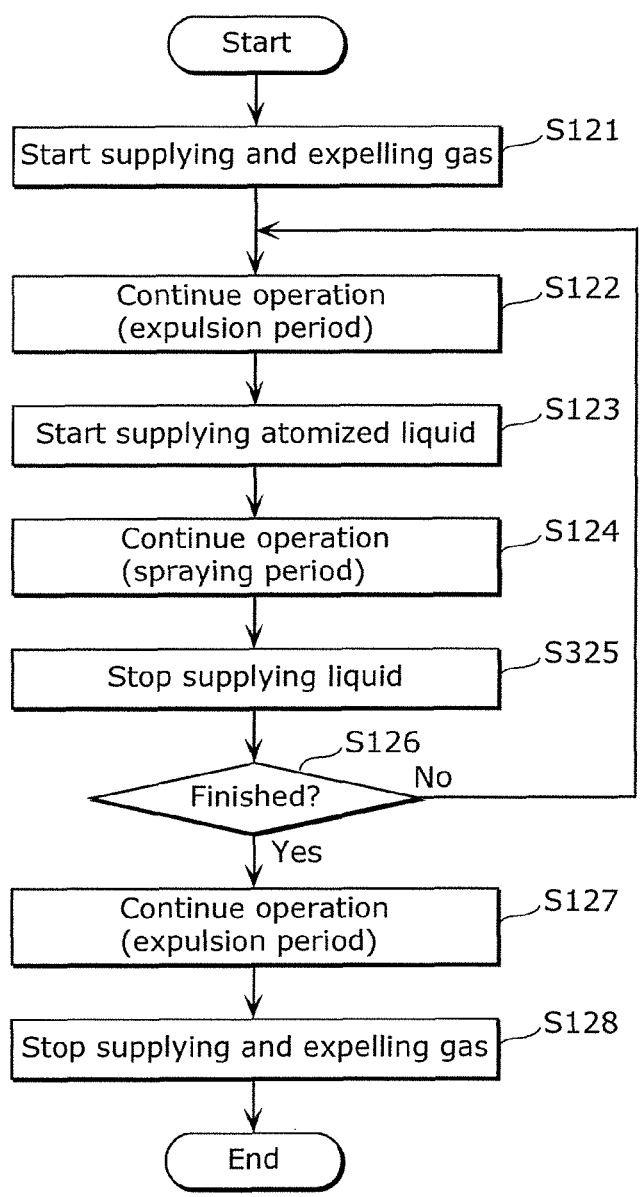
FIG. 5C is a flowchart showing another example of the sterilizing component removal method according to Embodiment 1.
Figure 6A:
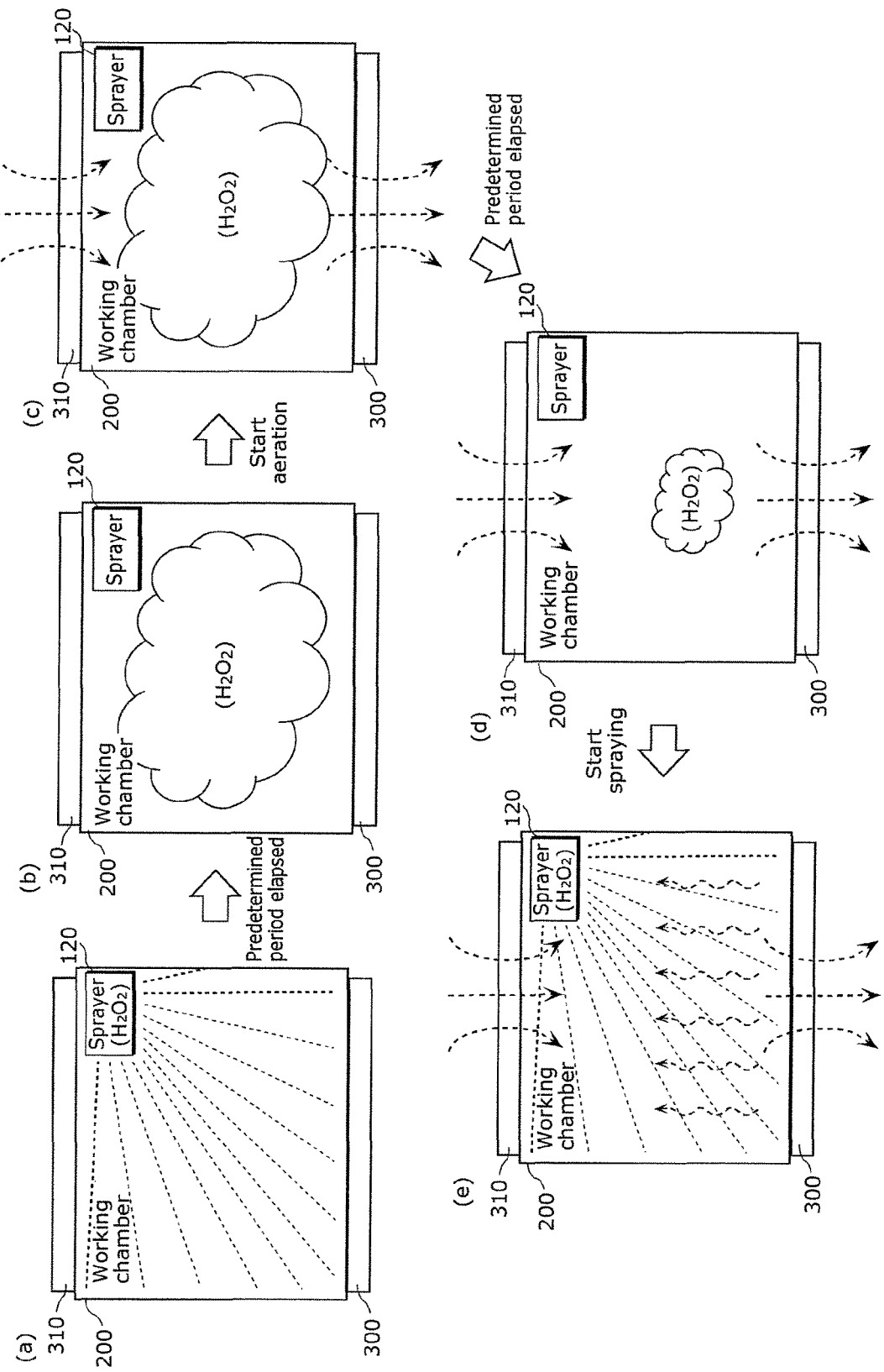
FIG. 6A illustrates internal states of the working chamber in process steps, which is included in the disinfected environment maintaining system according to Embodiment 1.
Figure 6B:
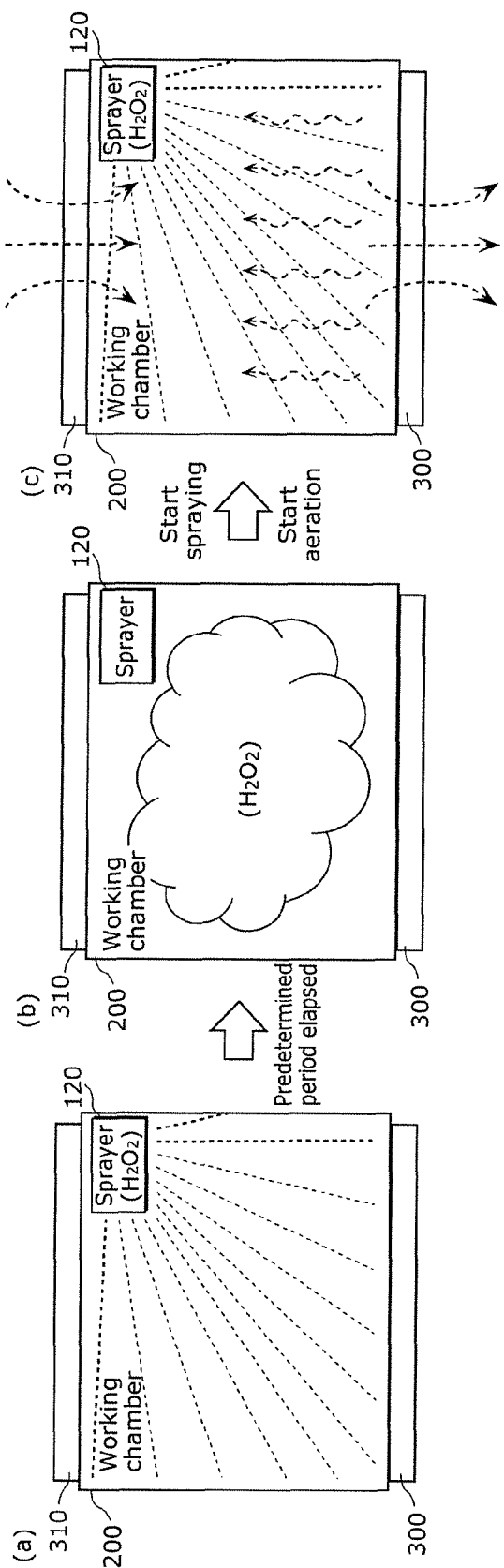
FIG. 6B illustrates internal states of the working chamber in process steps, which is included in the disinfected environment maintaining system according to Embodiment 1.

The following describes a third mode of the sterilizing component removal method according to the present exemplary embodiment, with reference to FIGS. 5C and 6C. In the third mode, an atomized liquid is supplied intermittently while gas is being expelled.

FIG. 5C is a flowchart showing the third mode of the sterilizing component removal method according to the present exemplary embodiment. FIG. 6C illustrates internal states of the working chamber 200 in process steps in the third mode. It should be noted that the processing until the spraying period elapses (up to S124) is the same as that in the first mode, and thus a description thereof is omitted (see FIG. 4 and (a) to (e) of FIG. 6C).

As shown in FIG. 5C, the atomized liquid is sprayed for the predetermined spraying period, and thereafter only the supply of the atomized liquid is stopped (S325). Specifically, as illustrated in (d) of FIG. 6C, the sprayer 120 stops spraying the liquid in a state where the supply device 310 continues supplying gas into the working chamber 200 and the expulsion device 300 continues expelling gas from the working chamber 200. In this manner, the sterilizing component gasified due to the spray of the atomized liquid is expelled outside the working chamber 200.

If the process of removing the sterilizing component has not been finished (No in S126), start spraying (S123), continue operation (S124), and stop spraying (S325) are repeated while aeration is kept performed (S122). A criterion for determination as to whether removal processing ends is, for example, a time elapsed from the start of the removal processing. For example, removal processing ends when a predetermined period elapses after the start of the removal processing.

Alternatively, a criterion for such determination may be the number of times an atomized liquid is sprayed. For example, the removal processing may end after the liquid is sprayed for a predetermined number of times. In addition, the criterion for such determination may be a concentration of the sterilizing component. For example, the disinfected environment maintaining system 10 may include a sensor which measures the concentration of the sterilizing component. In this case, disinfection processing may end if a sufficient fall of the concentration of the sterilizing component is detected.

If disinfection processing ends (Yes in S126), the operation is continued for a certain period (S127), gas supply and gas expulsion are stopped (S128). It should be noted that the reason why the current state is maintained for a certain time is to expel the sterilizing component gasified due to the liquid sprayed the last time.

As described above, in the third mode, a gas expulsion step, namely, the expulsion period (S122) and a liquid supply step, namely, the spraying period (S124) are repeated.

In this manner, a liquid is sprayed intermittently while gas is being expelled, and thus gasification of the sterilizing component is promoted and simultaneously gas can be expelled effectively. Accordingly, a time for removing the sterilizing component can be reduced.

[4-4. Fourth Mode (Gas Flow Condition)]

Figure 5D:
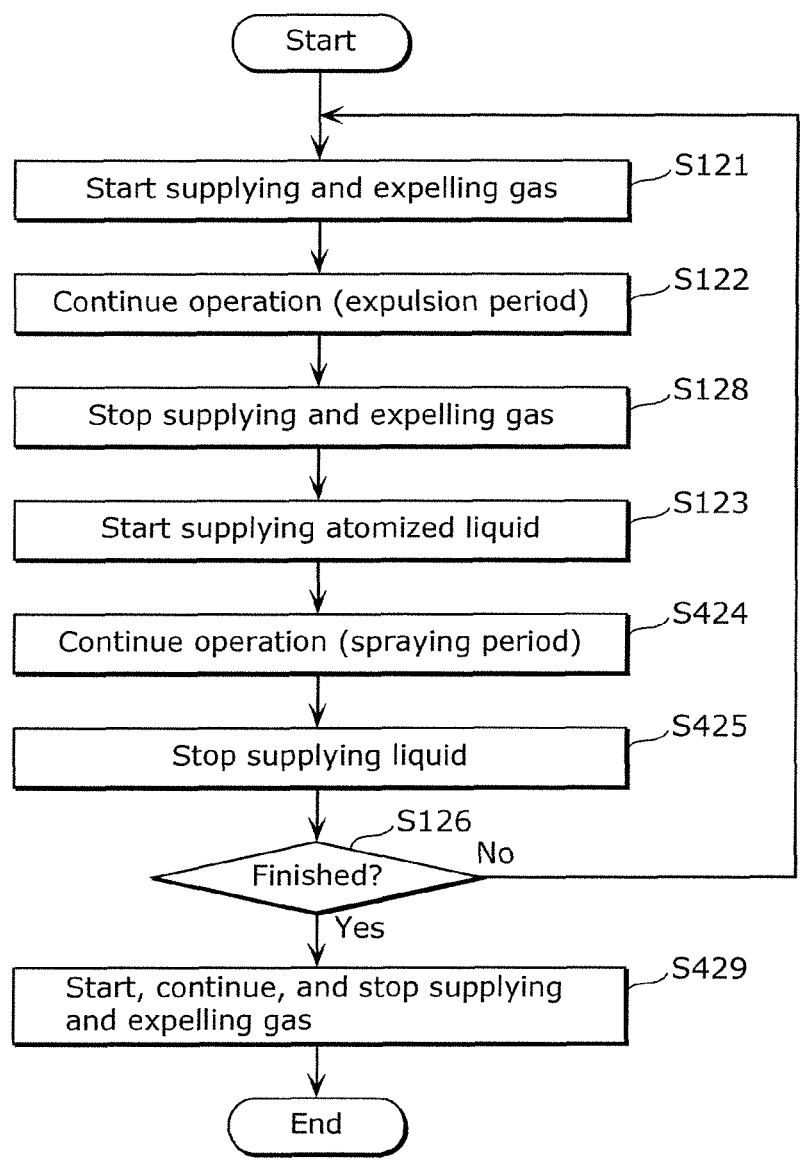
FIG. 5D is a flowchart showing another example of the sterilizing component removal method according to Embodiment 1.
Figure 6D:
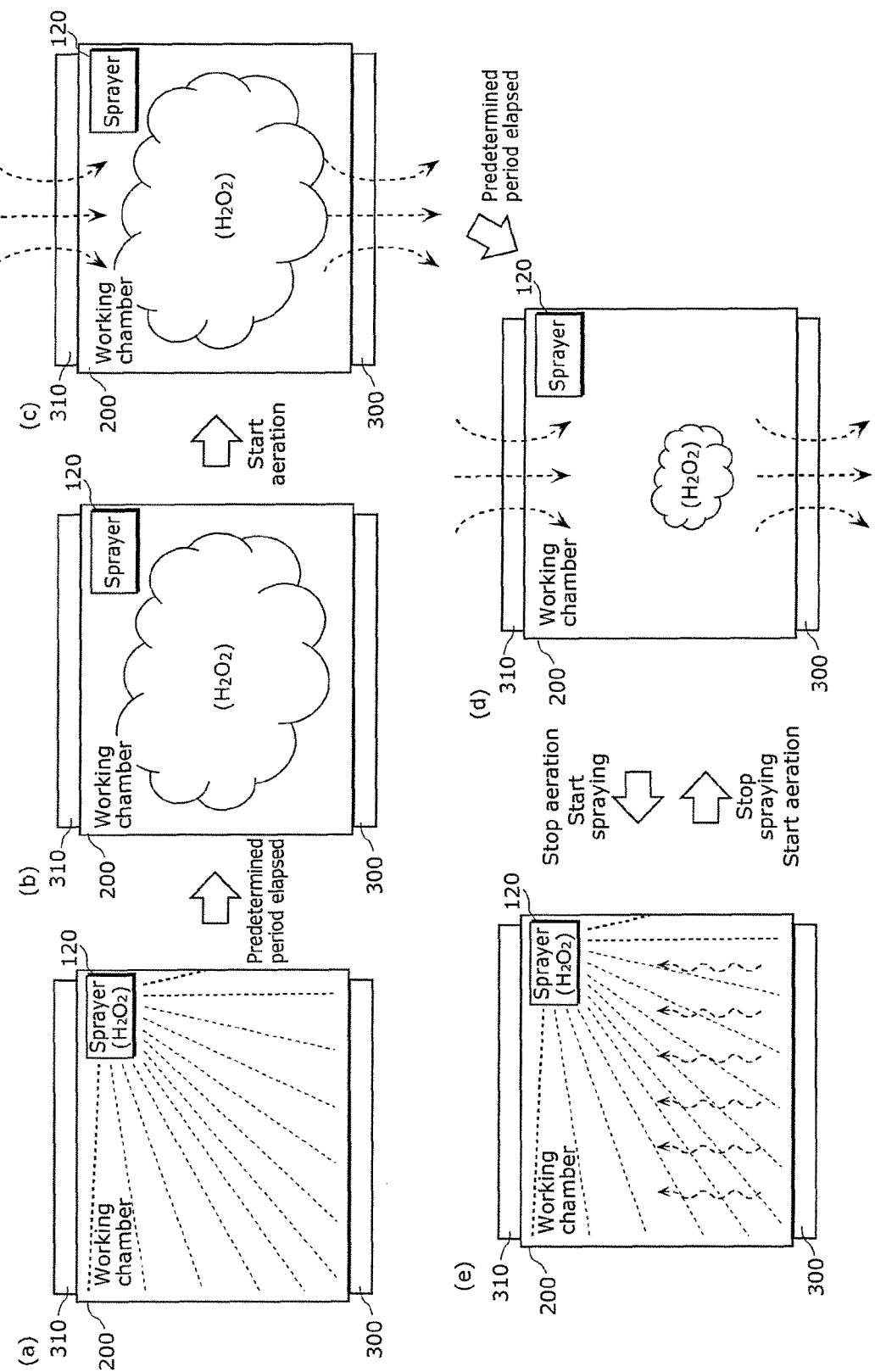
FIG. 6D illustrates internal states of the working chamber in process steps, which is included in the disinfected environment maintaining system according to Embodiment 1.

The following describes a fourth mode of the sterilizing component removal method according to the present exemplary embodiment, with reference to FIGS. 5D and 6D. In the fourth mode, a gas flow condition for when the sterilizing component is sprayed and a gas flow condition for when an atomized liquid is sprayed are the same.

FIG. 5D is a flowchart showing the fourth mode of the sterilizing component removal method according to the present exemplary embodiment. FIG. 6D illustrates internal states of the working chamber 200 in process steps in the fourth mode. It should be noted that the processing until the expulsion period elapses is the same as that in the first mode (to S122), and thus a description thereof is omitted (see FIG. 4 and (a) to (d) of FIG. 6D).

As shown in FIG. 5D, gas is expelled for the predetermined expulsion period, and thereafter gas supply and gas expulsion are stopped (S128). Specifically, the supply device 310 stops supplying gas into the working chamber 200, and the expulsion device 300 stops expelling gas from the working chamber 200 to the outside.

Then, as illustrated in (e) of FIG. 6D, the sprayer 120 starts spraying an atomized liquid (S123). Then, this operation is continued for a predetermined spraying period (S424). Since aeration is stopped, only the atomized liquid is sprayed into the working chamber 200 during the spraying period. Then, the sprayer 120 stops spraying the liquid after the spraying period elapses (S425).

If processing of removing the sterilizing component is not finished (No in S126), aeration (S121, S122, and S128) and spraying an atomized liquid (S123, S424, and S425) are repeated.

If disinfection processing ends (Yes in S126), gas supply and gas expulsion are continued for a certain period and thereafter stopped (S429).

As described above, in the fourth mode, the atomized liquid is supplied into the working chamber 200 in a state where a gas flow in the working chamber 200 is the same as the gas flow created when the sterilizing component is supplied into the working chamber 200, in the liquid supply step, namely, during the spraying period (S424).

Specifically, as illustrated in (a) and (e) of FIG. 6D, the gas flow in the working chamber 200 is the same in a period during which the sprayer 120 sprays the sterilizing component and a period during which the sprayer 120 sprays a liquid. For example, aeration is stopped while the sterilizing component is sprayed and a liquid is sprayed. At this time, as described above, gas is slightly supplied and gas is slightly expelled actually, thus circulating air between the inside and outside of the working chamber 200. In this manner, the sterilizing component and the atomized liquid are sprayed with almost no gas flow in the working chamber 200.

This allows the sterilizing component and the atomized liquid to be sprayed at almost the same area, thus increasing the probability that the sterilizing component and the liquid come into contact. Accordingly, gasification of the sterilizing component is further promoted, and a time for removing the sterilizing component can be reduced.

[5. Advantageous Effects and Others]

Figure 7A:
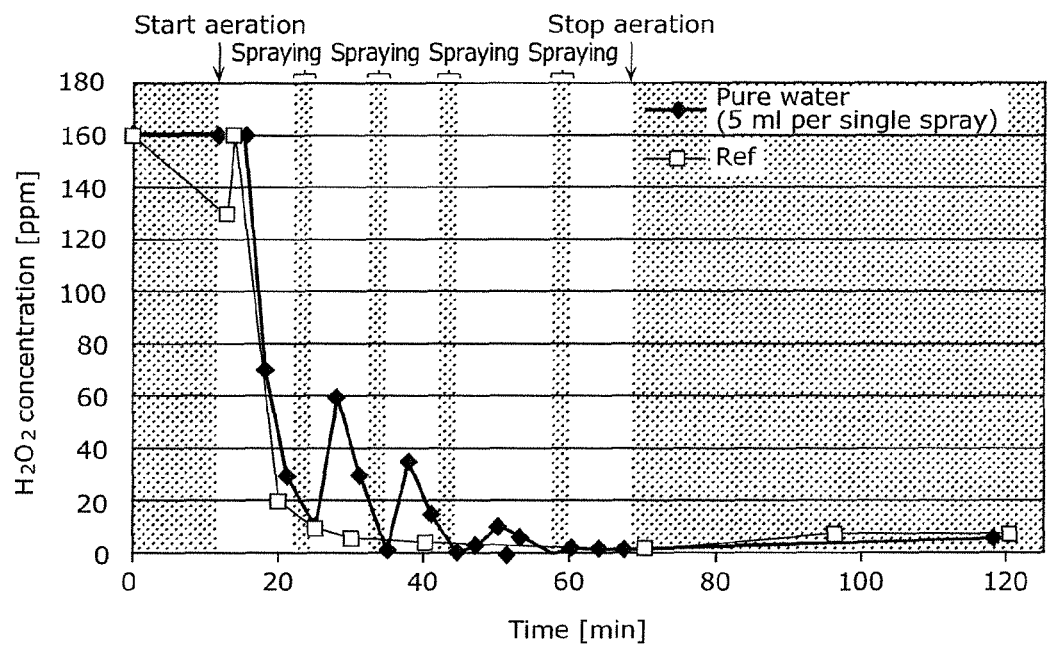
FIG. 7A illustrates a temporal change in a hydrogen peroxide concentration according to Embodiment 1.
Figure 7B:
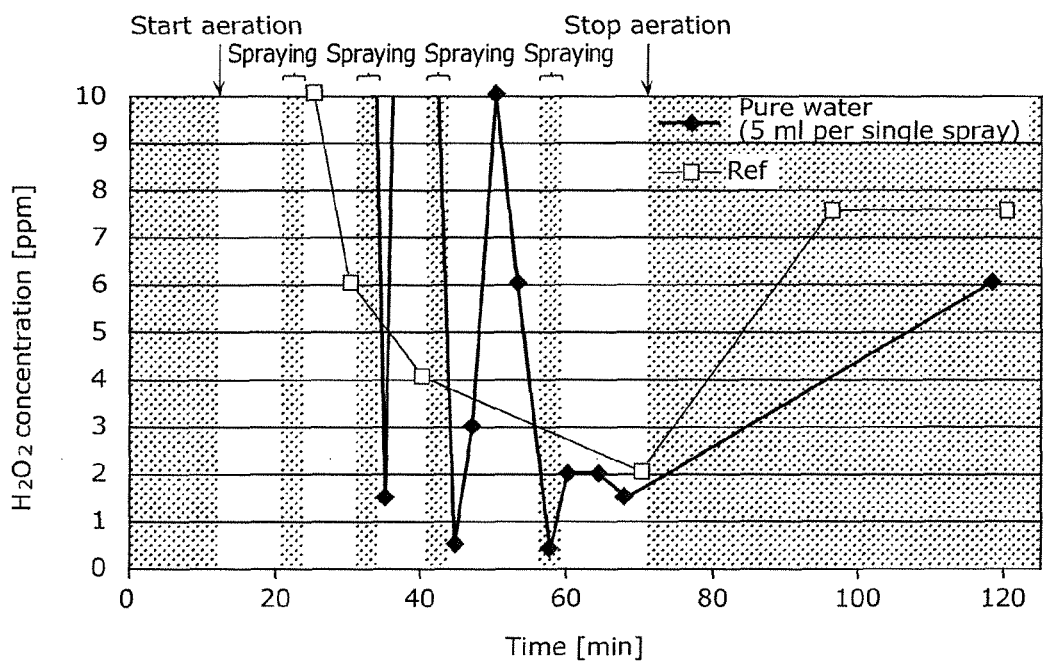
FIG. 7B is an enlarged view of a portion of the drawing illustrating the temporal change in the hydrogen peroxide concentration according to Embodiment 1.

The following describes advantageous effects achieved by the sterilizing component removal device 110 according to the present exemplary embodiment, with reference to FIGS. 7A and 7B. FIG. 7A illustrates a temporal change in a hydrogen peroxide concentration according to the present exemplary embodiment, and FIG. 7B is an enlarged view of a portion of FIG. 7A. Specifically, FIG. 7B illustrates a hydrogen peroxide concentration in a range of 0 ppm to 10 ppm in FIG. 7A.

FIGS. 7A and 7B illustrate a concentration of the sterilizing component (hydrogen peroxide) when the sterilizing component is removed in the third mode. Aeration is performed during a period from about the 12th minute to about the 65th minute, and the atomized liquid is sprayed four times in this period. The liquid sprayed is about 5 ml of pure water, and spraying the liquid lasts about 3 minutes. In addition, a hydrogen peroxide concentration indicates a concentration of hydrogen peroxide in the working chamber 200.

It should be noted that the amount of the liquid sprayed depends on the capacity of the working chamber 200, for example. Specifically, the greater the capacity of the working chamber 200 is, the greater amount of the liquid the sprayer 120 sprays. For example, the amount of the liquid sprayed may be proportional to the capacity of the working chamber 200. For example, the sprayer 120 sprays a 5-ml liquid, if the capacity of the working chamber 200 is 20 liters.

As illustrated in FIG. 7A, the hydrogen peroxide concentration rapidly decreases at substantially the same time as the start of aeration. Further, every time the atomized liquid is sprayed, the hydrogen peroxide concentration increases. This shows that liquefied hydrogen peroxide has been gasified by spraying the atomized liquid. Gasified hydrogen peroxide is expelled outside the working chamber 200 by aeration, and thus the hydrogen peroxide concentration decreases immediately after the increase.

The amount of increase in hydrogen peroxide concentration decreases each time the atomized liquid is sprayed. Thus, it can be seen that the amount of hydrogen peroxide to be gasified, or in other words, the amount of liquefied hydrogen peroxide decreases. Also, it can be seen that after the liquid is sprayed four times, the hydrogen peroxide concentration shows almost no increase, and the amount of liquefied hydrogen peroxide is sufficiently reduced.

It should be noted that after aeration is stopped, as illustrated in FIG. 7B, the remaining hydrogen peroxide partially gasifies, and the hydrogen peroxide concentration increases. However, finally the hydrogen peroxide concentration obtained when the liquid is sprayed (about 6 ppm) is lower than the hydrogen peroxide concentration obtained when the liquid is not sprayed (about 7.5 ppm).

As described above, the sterilizing component removal device 110 according to the present exemplary embodiment which removes the sterilizing component sprayed in the working chamber 200 having the outlet 201 includes the sprayer 120 which supplies, into the working chamber 200, an atomized liquid different from the sterilizing component. In addition, the sterilizing component removal method according to the present exemplary embodiment for removing the sterilizing component sprayed in the working chamber 200 having the outlet 201 includes supplying, into the working chamber 200, an atomized liquid different from the sterilizing component.

This promotes gasification of the sterilizing component with the atomized liquid, thus expelling the gasified sterilizing component through the outlet 201. Accordingly, the sterilizing component can be removed in a shorter time.

In addition, for example, the sprayer 120 may supply, into the working chamber 200, the atomized liquid which includes a substance which promotes gasification of the liquefied sterilizing component.

This achieves a reduction in time for removing the sterilizing component, since the liquid includes a substance which promotes gasification.

In addition, the disinfection device 100 according to the present exemplary embodiment includes the sterilizing component removal device 110, and the sprayer 120 further supplies an atomized sterilizing component into the working chamber 200.

Accordingly, a single sprayer 120 sprays the sterilizing component and the liquid, and thus the sterilizing component and the liquid can be sprayed in a similar manner. Specifically, the sterilizing component and the liquid can be sprayed on substantially the same area. Thus, a probability that the liquid and the sterilizing component come into contact can be increased, and gasification of the sterilizing component can be promoted by the liquid.

Furthermore, the disinfected environment maintaining system 10 according to the present exemplary embodiment includes the sterilizing component removal device 110 or the disinfection device 100, the working chamber 200, and the expulsion device 300 which expels gas from the working chamber 200 through the outlet 201.

This allows gas, or specifically, the gasified sterilizing component to be efficiently expelled from the working chamber 200, and thus a time for removing the sterilizing component can be reduced.

For example, the disinfected environment maintaining system 10 further includes the supply device 310 which supplies gas into the working chamber 200.

In this manner, a gas flow can be generated in the working chamber 200, and gas can be expelled more efficiently from the working chamber 200.

Embodiment 2

[1. Overview of Disinfected Environment Maintaining System]

Figure 8:
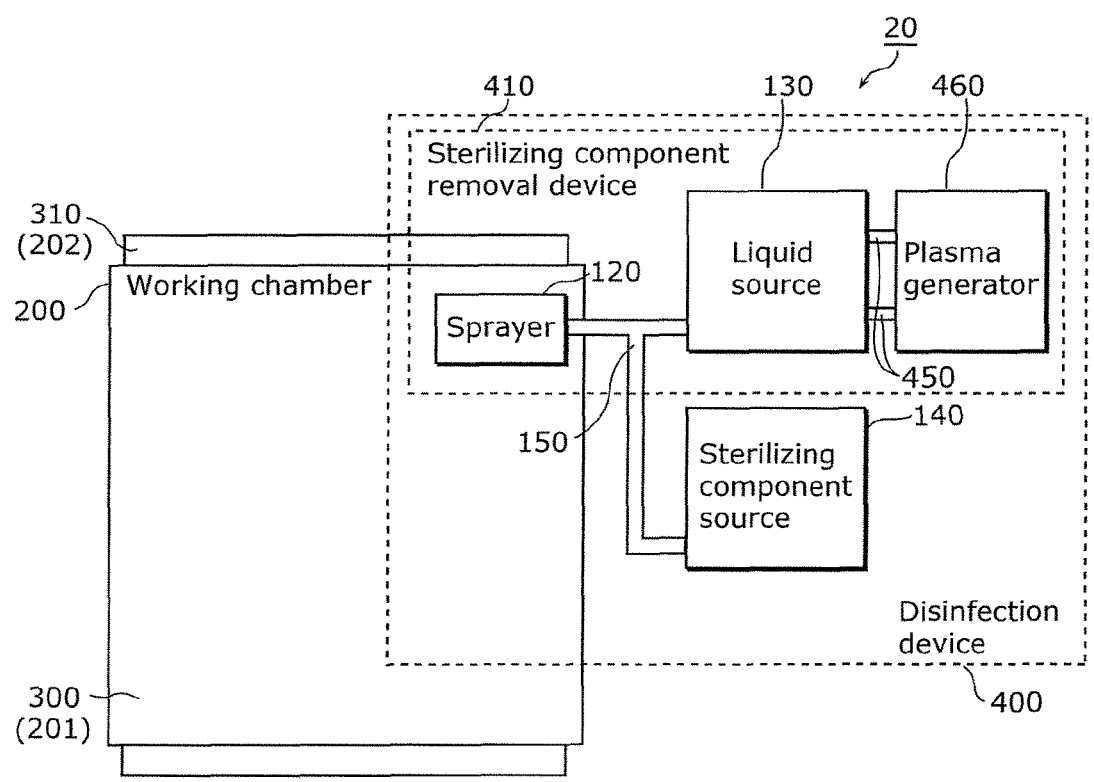
FIG. 8 is a configuration diagram illustrating a disinfected environment maintaining system according to Embodiment 2.

The first describes an overview of a disinfected environment maintaining system according to Embodiment 2, with reference to FIG. 8. FIG. 8 is a configuration diagram illustrating a disinfected environment maintaining system 20 according to the present exemplary embodiment. It should be noted that the following mainly describes differences from Embodiment 1.

The disinfected environment maintaining system 20 according to the present exemplary embodiment differs from the disinfected environment maintaining system 10 according to Embodiment 1 in that a disinfection device 400 is included instead of the disinfection device 100. Specifically, the difference is that the disinfection device 400 includes a sterilizing component removal device 410, instead of the sterilizing component removal device 110. As illustrated in FIG. 8, the sterilizing component removal device 410 differs from the sterilizing component removal device 110 illustrated in FIG. 1 in that piping parts 450 and a plasma generator 460 are newly included.

[1-1. Piping Parts]

The piping parts 450 are formed using tubular members such as pipes, tubes, or hoses, for example. The piping parts 450 connect the plasma generator 460 and the liquid source 130. In this configuration, the piping parts 450 form a circulation path for circulating a liquid stored in the liquid source 130. The plasma generator 460 is provided on this circulation path.

Specifically, the piping parts 450 supply the liquid stored in the liquid source 130 to the plasma generator 460, and supply the liquid treated by the plasma generator 460 (plasma treated liquid) to the liquid source 130.

[1-2. Plasma Generator]

The plasma generator 460 generates plasma in the liquid supplied through the piping part 450. The plasma generator 460 generates plasma in the liquid to supply an active species to the liquid. It should be noted that the plasma generator 460 may directly generate plasma in the liquid stored in the liquid source 130. Specifically, the sterilizing component removal device 410 may not include the piping parts 450.

For example, the plasma generator 460 includes a pair of ignition electrodes (a high-voltage electrode and a low-voltage electrode) disposed with a predetermined space therebetween. The pair of ignition electrodes are exposed inside the piping part 450. In other words, the pair of ignition electrodes are provided on the liquid circulation path. The plasma generator 460 applies, across the pair of ignition electrodes, a high voltage pulse having a negative polarity of 2 to 50 kV/cm and 100 Hz to 20 kHz, for example, thus discharging electricity into the liquid.

Air bubbles are generated near the pair of ignition electrodes in the liquid, through evaporation of moisture in the liquid by the energy of the electric discharge and gasification of moisture by a shock wave generated by the electric discharge. The plasma generator 460 generates plasma in the air bubbles, generates an active species using the generated plasma, and supplies the generated active species into the liquid.

Examples of the active species include hydroxyl radical (OH) (hereinafter, referred to as "OH radical"), ozone, superoxide anion ($O_2^-$), hydroperoxyl radical ($HO_2$), NO radical, nitrous acid ($HNO_2$), hydrogen radical (H), oxygen radical (O), monovalent oxygen ion ($O^-$), and others.

Furthermore, the plasma generator 460 not only supplies an active species, but supplies, to a liquid, a substance which promotes gasification of a sterilizing component. For example, the plasma generator 460 supplies nitric acid or the like to the liquid, when generating plasma.

In this manner, the liquid source 130 stores a liquid which includes an active species and a substance which promotes gasification of the sterilizing component. Specifically, the liquid source 130 stores plasma treated water which includes an OH radical and nitric acid. Accordingly, the sprayer 120 sprays plasma treated water inside the working chamber 200 in the present exemplary embodiment.

[2. Plasma Treated Water]

Figure 9:
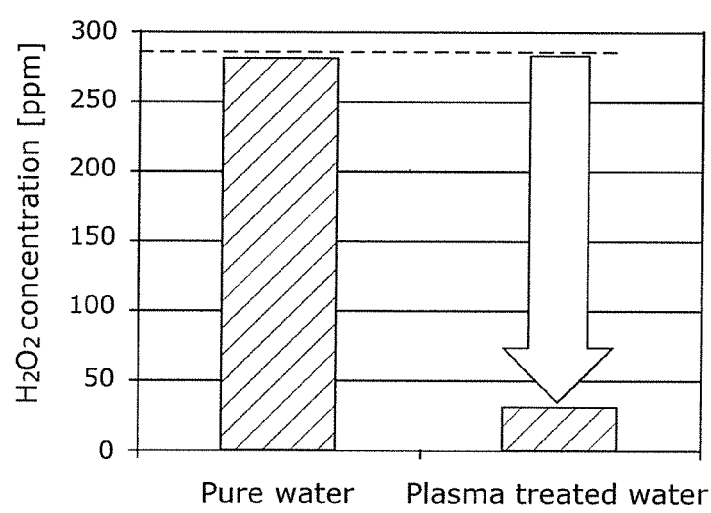
FIG. 9 illustrates an effect of reducing hydrogen peroxide by plasma according to Embodiment 2.

Here, a description is given of an effect of reducing the sterilizing component (hydrogen peroxide) achieved by plasma treated water according to the present exemplary embodiment, with reference to FIG. 9. FIG. 9 illustrates the effect of reducing hydrogen peroxide by plasma according to the present exemplary embodiment. Specifically, FIG. 9 illustrates results of measuring hydrogen peroxide concentrations after about 280 ppm hydrogen peroxide is supplied to 4 ml of pure water and plasma treated water, and the pure water and the plasma treated water are left for several minutes.

As illustrated in FIG. 9, a hydrogen peroxide concentration in pure water does not greatly change. In contrast, the hydrogen peroxide concentration in plasma treated water greatly decreases by merely being left for several minutes. This shows that plasma treated water promotes decomposition of hydrogen peroxide. Accordingly, the sterilizing component can be removed in a shorter time by decomposing hydrogen peroxide.

[3. Advantageous Effects and Others]

Figure 10A:
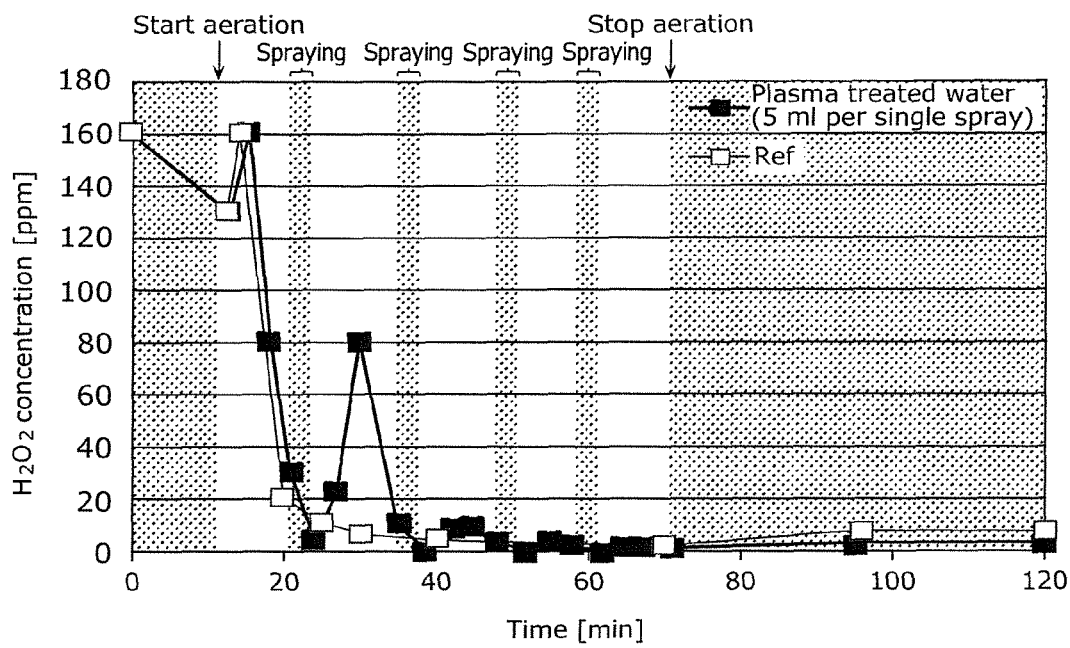
FIG. 10A illustrates a temporal change in a hydrogen peroxide concentration according to Embodiment 2.
Figure 10B:
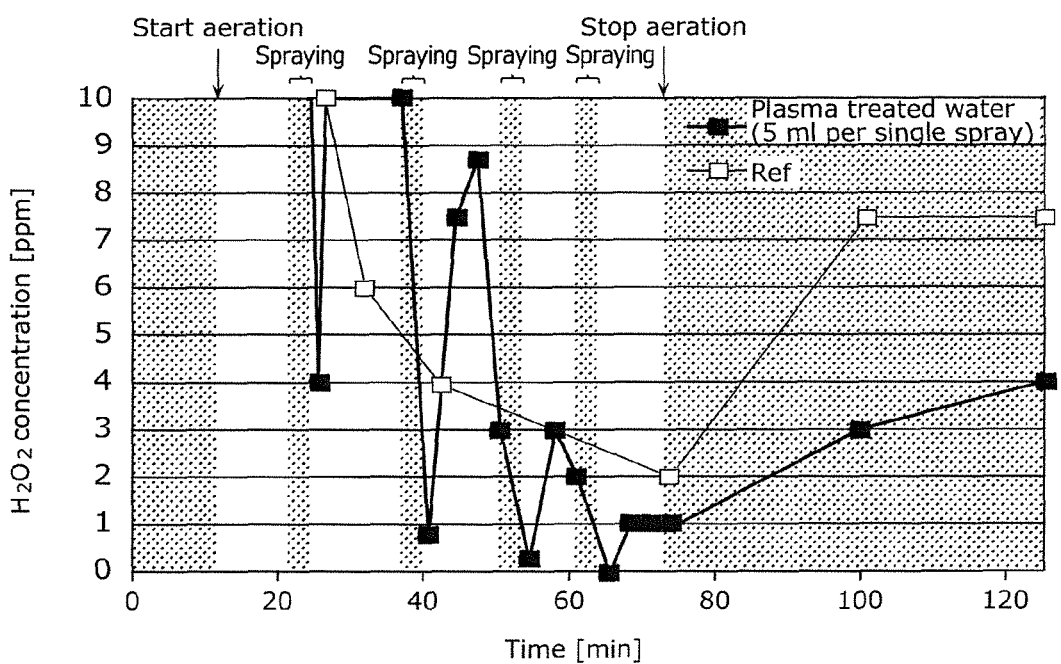
FIG. 10B is an enlarged view of a portion of the drawing illustrating the temporal change in the hydrogen peroxide concentration according to Embodiment 2.

The following describes advantageous effects achieved by the sterilizing component removal device 410 according to the present exemplary embodiment, with reference to FIGS. 10A and 10B. FIG. 10A illustrates a temporal change in hydrogen peroxide concentration according to the present exemplary embodiment, and FIG. 10B is an enlarged view of a portion of FIG. 10A. Specifically, FIG. 10B illustrates a hydrogen peroxide concentration in a range of 0 to 10 ppm in FIG. 10A.

FIGS. 10A and 10B illustrate the case where a sterilizing component is removed under the same condition as with the case of FIGS. 7A and 7B. As illustrated in FIG. 10A, a hydrogen peroxide concentration increases after atomized plasma treated water is sprayed.

Here, unlike the case of FIG. 7A, the hydrogen peroxide concentration shows almost no increase due to the plasma treated water sprayed for the second and subsequent times. Accordingly, it can be seen that spraying plasma treated water for the first time gasifies/decomposes more hydrogen peroxide than spraying pure water.

Furthermore, finally, a hydrogen peroxide concentration when plasma treated water is sprayed is lower than a hydrogen peroxide concentration when a liquid is not sprayed, as illustrated in FIG. 10B. As can be seen from a comparison with FIG. 7B, the hydrogen peroxide concentration obtained when plasma treated water is sprayed (about 4 ppm) is lower than the hydrogen peroxide concentration obtained when pure water is sprayed (about 6 ppm).

As described above, in the sterilizing component removal device 410 according to the present exemplary embodiment, the sprayer 120 supplies, into the working chamber 200, an atomized liquid which includes an active species which decomposes a sterilizing component.

This not only promotes gasification of the sterilizing component, but causes the active species to decompose the sterilizing component, thus achieving a reduction in time for removing the sterilizing component.

Furthermore, for example, the sterilizing component removal device 410 further includes the liquid source 130 which supplies a liquid to the sprayer 120, and the plasma generator 460 which generates plasma to generate an active species in the liquid stored in the liquid source 130.

Accordingly, the active species can be efficiently generated using plasma, and thus a time for removing the sterilizing component can be further reduced.

[4. Plasma Generator which Includes Gas Supply]

It should be noted that the plasma generator 460 may include a gas supply, in order to promote generating plasma. The gas supply is, for example, a pump or the like, and generates air bubbles in a liquid by supplying gas such as air into the liquid. The gas supply may supply, for example, helium gas, argon gas, or oxygen gas, instead of air.

Specifically, the gas supply supplies air between the pair of ignition electrodes of the plasma generator 460. Then, the plasma generator 460 discharges electricity into the air bubbles generated by the gas supply, to generate plasma. It should be noted that the gas supply starts supplying gas, before or simultaneously with the start of electric discharge by the plasma generator 460, for example.

Figure 11:
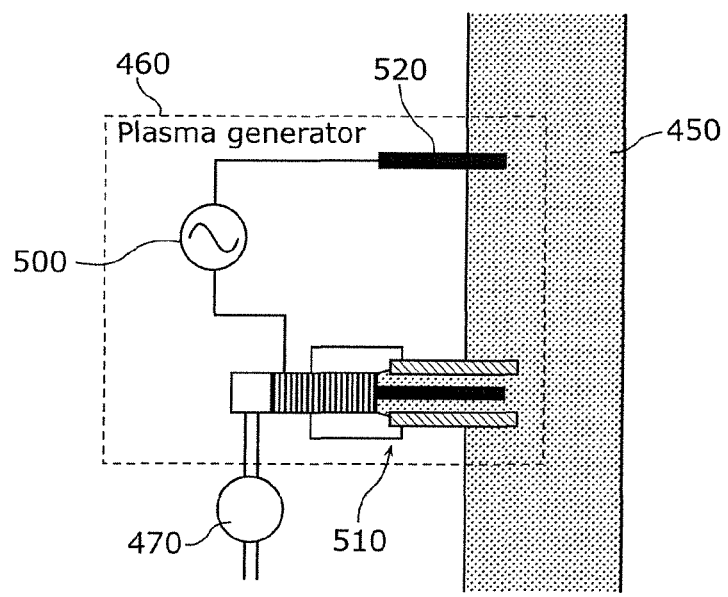
FIG. 11 is a configuration diagram illustrating an example of a plasma generator according to Embodiment 2.

Here, a description is given of a detailed configuration of the plasma generator 460 when the gas supply is included, with reference to FIG. 11. FIG. 11 is a configuration diagram illustrating the plasma generator 460 according to the present exemplary embodiment.

As illustrated in FIG. 11, the plasma generator 460 includes a power supply 500, a first electrode portion 510, and a second electrode portion 520.

The power supply 500 applies a voltage across the first electrode portion 510 and the second electrode portion 520.

For example, the power supply 500 applies a high voltage pulse having a negative polarity of 2 to 50 kV/cm and 100 Hz to 20 kHz, across the first electrode portion 510 and the second electrode portion 520.

The first electrode portion 510 is one of the pair of ignition electrodes. A portion of the first electrode portion 510 is exposed to a liquid. For example, the first electrode portion 510 is disposed penetrating through the wall of the piping part 450.

Furthermore, a gas supply 470 is connected to the first electrode portion 510. Gas supplied from the gas supply 470 appears as air bubbles near the portion of the first electrode portion 510 exposed to the liquid. A detailed configuration is described later with reference to FIGS. 12A and 12B.

The second electrode portion 520 is the other of the pair of ignition electrodes. A portion of the second electrode portion 520 is exposed to the liquid. For example, the second electrode portion 520 is disposed penetrating through the wall of the piping part 450. A high voltage is applied across the first electrode portion 510 and the second electrode portion 520, thus generating plasma in the liquid. It should be noted that the second electrode portion 520 includes copper, aluminum, or iron, for example.

Figure 12A:
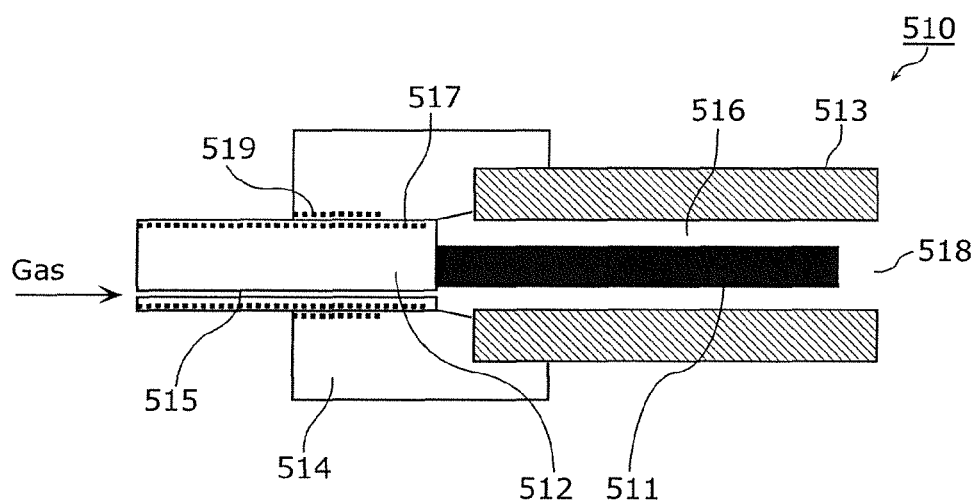
FIG. 12A is a configuration diagram illustrating an example of an electrode portion of the plasma generator according to Embodiment 2.

Here, a description is given of a detailed configuration of the first electrode portion 510, with reference to FIG. 12A. FIG. 12A illustrates an example of the electrode portion of the plasma generator 460 according to the present exemplary embodiment.

As illustrated in FIG. 12A, the first electrode portion 510 includes a metal electrode portion 511, a metal screw portion 512, an insulator 513, and a holding block 514.

The metal electrode portion 511 is disposed in the piping part 450, as illustrated in FIG. 11. Specifically, the metal electrode portion 511 is exposed to the liquid in the piping part 450. The metal electrode portion 511 is pressed into the metal screw portion 512 so as to be formed into a united portion. It should be noted that the metal electrode portion 511 is provided not projecting outward relative to an opening 518 of the insulator 513.

The metal electrode portion 511 is a rod member having a diameter of 0.95 mm, and includes tungsten, for example. It should be noted that the diameter of the metal electrode portion 511 is not limited to this. It is sufficient if the diameter allows generation of plasma, and may be 2 mm or less, for example. The material of the metal electrode portion 511 is not limited to tungsten, and may be other plasma-resistant metal material. Although durability decreases, the metal electrode portion 511 may include copper, aluminum, iron, or an alloy of such material.

The metal screw portion 512 is a rod member having a diameter of 3 mm, and includes iron, for example. It should be noted that the diameter of the metal screw portion 512 is not limited to this, and it is sufficient if the diameter is greater than that of the metal electrode portion 511, for example. Furthermore, the material of the metal screw portion 512 is also not limited to iron, and may be, for example, copper, zinc, aluminum, tin, or brass which is the material used for a typical screw. It should be noted that the metal screw portion 512 and the metal electrode portion 511 may include the same material and have the same size, or may include different materials and have different sizes.

A through hole 515 is formed in the metal screw portion 512. The through hole 515 communicates with a space 516 surrounded by the insulator 513. Gas supplied from the gas supply 470 is supplied to the space 516 through the through hole 515. Then, the metal electrode portion 511 is covered with the gas supplied via the through hole 515.

Here, if only a single through hole 515 is formed in the metal screw portion 512, the through hole 515 is formed such that gas is supplied from underneath the metal electrode portion 511 in the opposite direction of gravity. In this manner, the metal electrode portion 511 can be easily covered with gas. The diameter of the through hole 515 is 0.3 mm, for example.

The outer surface of the metal screw portion 512 has a threaded portion 517. For example, the threaded portion 517 is a male screw.

The insulator 513 is provided so as to surround the metal electrode portion 511. The insulator 513 forms the space 516 between the insulator 513 and the metal electrode portion 511. For example, the insulator 513 is a tubular member having an inside diameter of 1 mm. Although the insulator 513 includes, for example, alumina ceramic, the insulator 513 may include magnesia, quartz, yttrium oxide, or the like.

The insulator 513 has the opening 518. The opening 518 adjusts the size of air bubbles, when air bubbles are generated in the liquid inside the piping part 450. For example, the diameter of the opening 518 is equal to the inside diameter of the insulator 513, and is 1 mm.

It should be noted that the opening 518 is provided in the end surface of the insulator 513, but may be provided in the lateral surface thereof. Furthermore, a plurality of the openings 518 may be provided in the insulator 513.

As described above, the metal electrode portion 511 is covered with gas supplied from the gas supply 470 into the space 516, and thus the metal electrode portion 511 does not come into direct contact with the liquid in the piping part 450. Accordingly, the metal electrode portion 511 can readily discharge electricity and generate plasma.

The holding block 514 is a member for holding the metal screw portion 512 and the insulator 513. The holding block 514 has a threaded portion 519. The threaded portion 519 is, for example, a female screw, and screws onto the threaded portion 517 of the metal screw portion 512. Rotating the metal screw portion 512 allows adjustment of the positional relationship between the insulator 513 and the metal electrode portion 511.

As illustrated above, the gas supply 470 supplies gas near the connected end of one of the pair of ignition electrodes (the metal electrode portion 511) included in the plasma generator 460. Accordingly, the metal electrode portion 511 can be covered with gas, which allows discharging electricity and generation of plasma with ease.

Figure 12B:
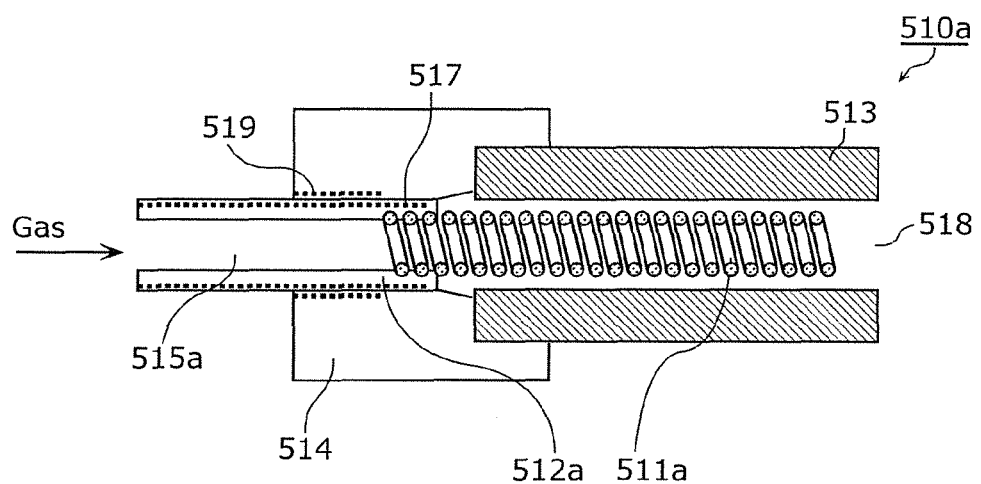
FIG. 12B is a configuration diagram illustrating another example of the electrode portion of the plasma generator according to Embodiment 2.

It should be noted that the plasma generator 460 according to the present exemplary embodiment may include a first electrode portion 510*a* illustrated in FIG. 12B, instead of the first electrode portion 510 described above.

The first electrode portion 510*a* illustrated in FIG. 12B differs from the first electrode portion 510 illustrated in FIG. 12A in that a metal electrode portion 511*a* and a metal screw portion 512*a* are included, instead of the metal electrode portion 511 and the metal screw portion 512. The following mainly describes the differences.

The metal electrode portion 511*a* is a hollow electrode. For example, the metal electrode portion 511*a* is a tungsten coiled electrode having 0.99 mm outer dimension. It should be noted that the metal electrode portion 511*a* is not limited to be coiled, and may be a hollow rod member.

The metal screw portion 512*a* has, in an axial center portion, a through hole 515*a* having, for example, a large diameter of 1 mm. The metal electrode portion 511*a* is connected being screwed in the through hole 515*a*, for example.

Accordingly, an increase in the size of the through hole 515a allows the through hole 515a to be formed with ease, and achieves a reduction in the manufacturing cost.

As described above, if the plasma generator 460 includes the gas supply 470, the plasma generator 460 generates plasma in air bubbles produced by the supplied gas, and thus can generate plasma efficiently. Accordingly, for example, the active species can be adequately supplied into a liquid in a short time.

Embodiment 3

[1. Overview of Disinfected Environment Maintaining System]

Figure 13A:
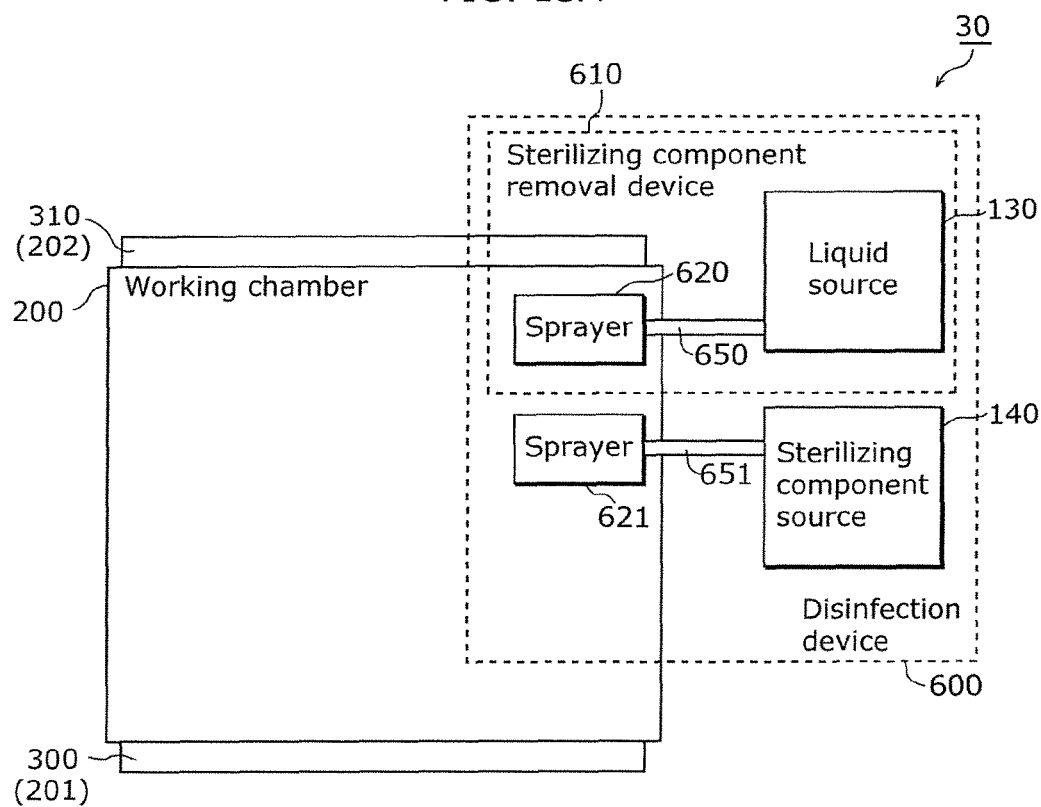
FIG. 13A is a configuration diagram illustrating an example of a disinfected environment maintaining system according to Embodiment 3.
Figure 13B:
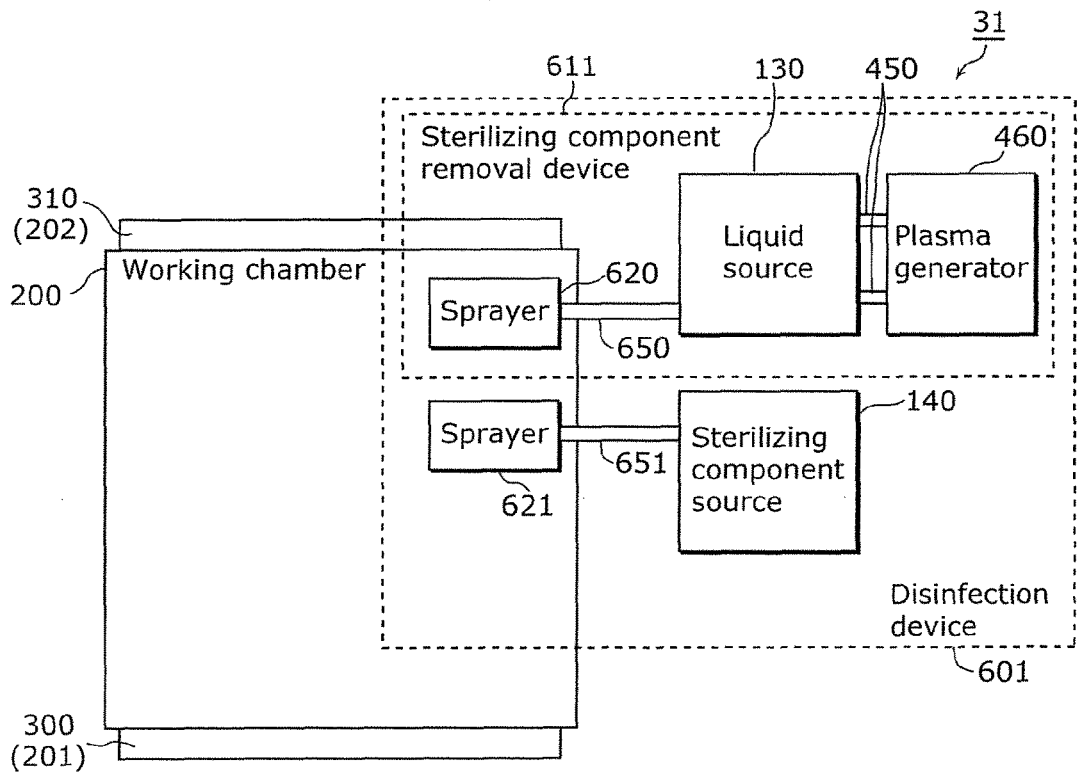
FIG. 13B is a configuration diagram illustrating another example of the disinfected environment maintaining system according to Embodiment 3.

The first describes the overview of a disinfected environment maintaining system according to Embodiment 3, with reference to FIGS. 13A and 13B. FIGS. 13A and 13B are configuration diagrams illustrating disinfected environment maintaining systems 30 and 31 according to the present exemplary embodiment, respectively.

The number of sprayers included in the disinfected environment maintaining systems 30 and 31 illustrated in FIGS. 13A and 13B is different from that of the disinfected environment maintaining systems 10 and 20 according to Embodiments 1 and 2.

Specifically, the difference is that the disinfected environment maintaining systems 30 and 31 include disinfection devices 600 and 601, respectively, instead of the disinfection devices 100 and 400.

More specifically, the difference is that instead of the sterilizing component removal devices 110 and 410, the disinfection devices 600 and 601 include sterilizing component removal devices 610 and 611, respectively, and each newly include a sprayer 621 and a piping part 651. The sterilizing component removal devices 610 and 611 each include a sprayer 620 and a piping part 650, instead of the sprayer 120 and the piping part 150.

[1-1. Sprayers]

The sprayer 620 is an example of a first sprayer which supplies an atomized liquid different from a sterilizing component into a working chamber 200. Unlike the sprayer 120, the sprayer 620 sprays only an atomized liquid, but not the sterilizing component.

For example, the sprayer 620 illustrated in FIG. 13A sprays atomized pure water, whereas the sprayer 620 illustrated in FIG. 13B sprays atomized plasma treated water.

The sprayer 621 is an example of a second sprayer which supplies an atomized sterilizing component into the working chamber 200. For example, the sprayer 621 includes a spray nozzle, and sprays (mists) a fine atomized sterilizing component of several to tens of microns into the working chamber 200.

Specifically, a liquid sterilizing component stored in a sterilizing component source 140 is supplied to the sprayer 621 through the piping part 651. Then, the sprayer 621 atomizes the supplied liquid sterilizing component, and sprays the atomized component into the working chamber 200.

[1-2. Piping Parts]

The piping parts 650 and 651 are formed using tubular members, such as pipes, tubes, or hoses, for example. The piping part 650 connects the sprayer 620 and a liquid source 130. The piping part 651 connects the sprayer 621 and the sterilizing component source 140.

Accordingly, only a liquid (pure water or plasma treated water) from the liquid source 130 flows through the piping part 650. Furthermore, only a sterilizing component from the sterilizing component source 140 flows through the piping part 651. Accordingly, the liquid and the sterilizing component can be prevented from coming into contact in the piping parts, unlike Embodiments 1 and 2.

[2. Advantageous Effects and Others]

As described above, the disinfection devices 600 and 601 according to the present exemplary embodiment include the sterilizing component removal devices 610 and 611, respectively, and each include the sprayer 621 which supplies an atomized sterilizing component into the working chamber 200.

This prevents the sterilizing component and the liquid from coming into contact before being sprayed, and thus promoting effects achieved by the liquid can be further increased. Accordingly, the time for removing the sterilizing component can be further reduced.

If the liquid is plasma treated water, the plasma treated water decomposes the sterilizing component by coming into contact with the sterilizing component. In contrast, as illustrated in FIG. 13B, since the disinfection device 601 includes two sprayers and two piping parts, thus preventing the sterilizing component from coming into contact with plasma treated water before spraying the sterilizing component, and the fall of sterilizing properties of the sterilizing component can be inhibited.

Variation

Figure 14A:
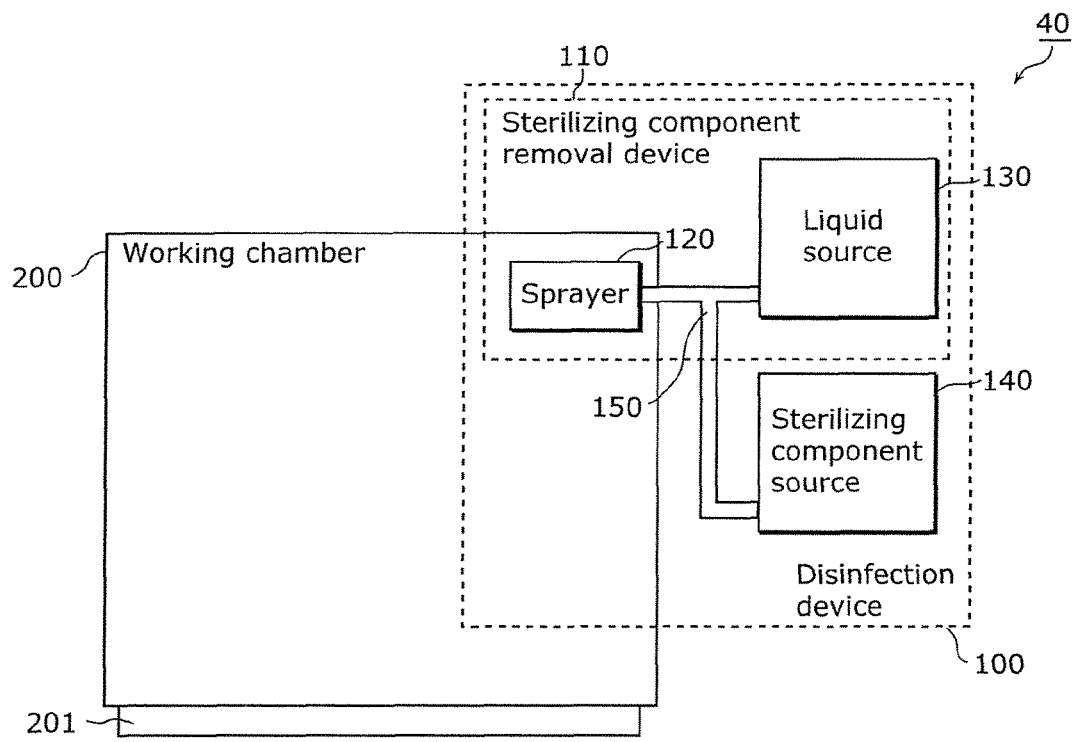
FIG. 14A is a configuration diagram illustrating an example of a disinfected environment maintaining system according to a variation of exemplary embodiments.
Figure 14B:
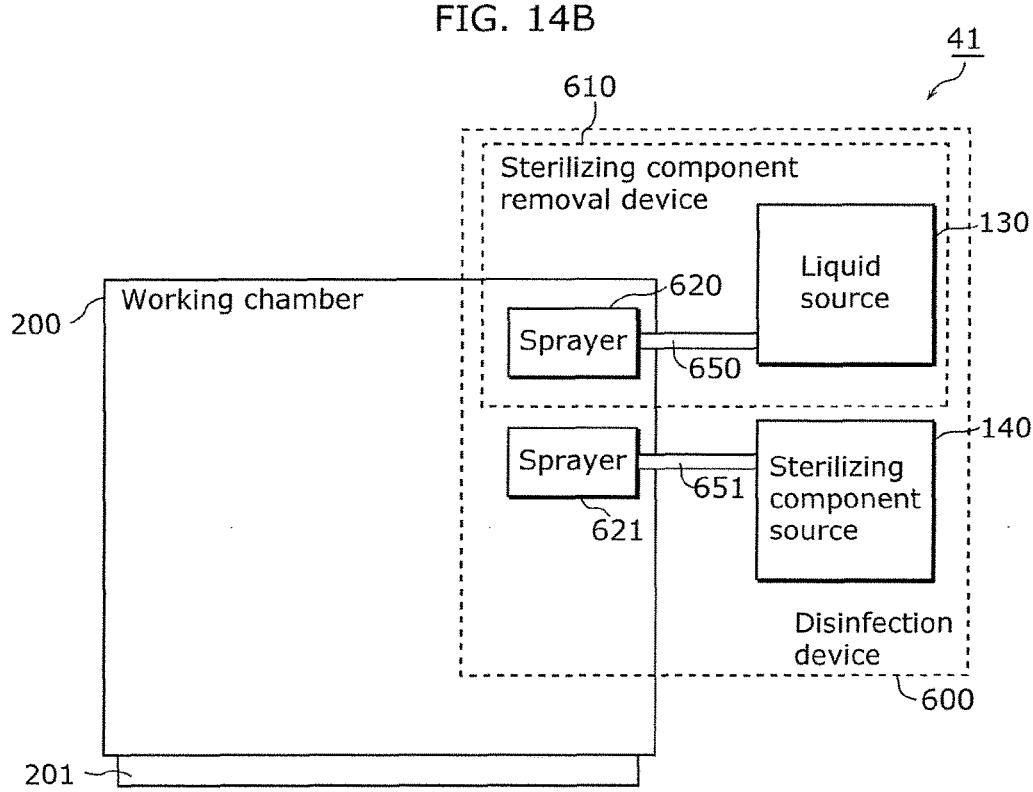
FIG. 14B is a configuration diagram illustrating another example of the disinfected environment maintaining system according to the variation of the exemplary embodiments.

The following describes a variation of the disinfected environment maintaining system according to the above exemplary embodiments, with reference to FIGS. 14A and 14B. FIGS. 14A and 14B are configuration diagrams illustrating disinfected environment maintaining systems 40 and 41 according to this variation, respectively.

The disinfected environment maintaining systems 40 and 41 according to this variation differ from the disinfected environment maintaining systems 10 and 30 illustrated in FIGS. 1 and 13A in that the expulsion device 300 and the supply device 310 are not included. Specifically, the disinfected environment maintaining systems 40 and 41 according to this variation do not perform aeration.

Even in this case, a gasified sterilizing component is expelled outside the working chamber 200 through an outlet 201. Spraying a liquid can promote gasification of a sterilizing component, and thus the sterilizing component can be removed in a shorter time than in the case where the liquid is not sprayed.

Other Exemplary Embodiments

Although the above has described the sterilizing component removal device, the disinfection device, the disinfected environment maintaining system, and the sterilizing component removal method according to one or more aspects, based on the exemplary embodiments, the present disclosure is not limited to such embodiments. The scope of the present disclosure also includes various modifications made to the embodiments and aspects achieved by combining constituent elements in different embodiments, which may be conceived by those skilled in the art, without departing from the essence of the present disclosure.

For example, Embodiment 1 above has described the case where the sterilizing component removal device 110 includes only one sprayer 120, but the present disclosure is not limited to this. The sterilizing component removal device 110 may include a plurality of the sprayers 120. Unlike Embodiment 3, the sprayers 120 are connected to the liquid source 130 (and the sterilizing component source 140) in this case, and spray a liquid (and a sterilizing component). This can increase the spray volume per unit time.

For example, Embodiment 1 above has described the configuration in which the sterilizing component removal device 110 includes one liquid source 130 and one sterilizing component source 140, but the configuration is not limited to this. The number of liquid sources 130 or sterilizing component sources 140 included in the sterilizing component removal device 110 or the numbers of liquid sources 130 and sterilizing component sources 140 included therein may be plural.

For example, the sterilizing component removal device 110 may include a plurality of the liquid sources 130 and a plurality of the sterilizing component sources 140. At this time, the sprayer 120 may select and spray a liquid or a sterilizing component.

For example, the liquid sources 130 can store different liquids. The liquids stored in the liquid sources 130 correspond to sterilizing components stored in the sterilizing component sources 140, for example. Specifically, the liquids stored in the liquid sources 130 have high effects of promoting gasification of corresponding sterilizing components.

For example, as described above, if a hydrogen peroxide solution is used as a sterilizing component, water containing nitric acid is used as a liquid for promoting gasification. Alternatively, if formalin (which has a boiling point of about 100 degrees) is used as a sterilizing component, alcohol having a lower boiling point can be used as a liquid for promoting gasification. At this time, formalin can also be decomposed by using hypochlorous acid. Furthermore, if peracetic acid (which has a boiling point of about 105 degrees) is used as a sterilizing component, water or alcohol can be used as a liquid for promoting gasification. It should be noted that ethylene oxide can also be decomposed by using water.

In this manner, a liquid can be changed according to the sterilizing component to be used, and thus a liquid having a high effect of promoting gasification can be used. Accordingly, gasification of the sterilizing component can be further promoted and the time for removing the sterilizing component can be reduced.

Furthermore, for example, the above embodiments have described the configuration in which the liquid source 130 and the sterilizing component source 140 supply a liquid and a sterilizing component to sprayer 120, for instance, but the present disclosure is not limited to this. For example, the sprayer 120 may obtain a liquid and a sterilizing component by pumping up the liquid and the sterilizing component from the liquid source 130 and the sterilizing component source 140. In this case, the sprayer 120 alternatively selects either the liquid source 130 or the sterilizing component source 140, and obtains the liquid or the sterilizing component.

Furthermore, for example, in Embodiment 2 above, an active species is supplied into the liquid using the plasma generator 460, but the present disclosure is not limited to this. An active species may be generated using, for instance, heat, light, or radiation, rather than plasma.

For example, the above exemplary embodiments have described an example in which the sprayer 120 is included at the upper part of the working chamber 200, but the present disclosure is not limited to this. As long as the sprayer 120 can spray a liquid or a sterilizing component in the working chamber 200, the sprayer 120 may be disposed anywhere. For example, the sprayer 120 may be disposed at the lower part of the working chamber 200, and spray a liquid or a sterilizing component upwards. Alternatively, the sprayer 120 may be disposed near the inlet 202. In this case, the sprayed liquid or sterilizing component can be supplied into the working chamber 200 along the gas flow generated by aeration.

Various changes, replacement, addition, omission, and others can be made to the above embodiments within the scope and an equivalent scope of the claims.

INDUSTRIAL APPLICABILITY

The present disclosure is applicable as a sterilizing component removal device, a disinfection device, a disinfected environment maintaining system, and a sterilizing component removal method which can remove a sterilizing component in a shorter time, and is applicable to, for example, a culture device for cells and others, a glove box, an incubator, and so on.

The invention claimed is:

1. A sterilizing component removal device which removes a sterilizing component sprayed in a working chamber having an outlet, the sterilizing component removal device comprising:
   a sprayer which is disposed in the working chamber and which supplies, in an atomized manner, a liquid different from the sterilizing component into the working chamber so as to promote gasification of the sterilizing component;
   a liquid source for supplying the liquid to the sprayer; and
   a sterilizing component source for supplying the sterilizing component to the sprayer,
   wherein the sprayer sprays, in the working chamber, the liquid in the atomized manner separately from the sterilizing component.

2. The sterilizing component removal device according to claim 1, wherein the sprayer supplies, in the atomized manner, the liquid which includes a substance which promotes gasification of the sterilizing component which is liquefied, into the working chamber.

3. The sterilizing component removal device according to claim 1, wherein the sprayer supplies, in the atomized manner, the liquid which includes an active species which decomposes the sterilizing component, into the working chamber.

4. The sterilizing component removal device according to claim 3, further comprising:
   a plasma generator which generates plasma to generate the active species in the liquid stored in the liquid source.

5. A disinfection device comprising:
   the sterilizing component removal device according to claim 1,
   wherein the sprayer further supplies, in the atomized manner, the sterilizing component into the working chamber.

6. A disinfected environment maintaining system comprising:
   the sterilizing component removal device according to claim 1;
   the working chamber; and
   an expulsion device which expels gas from the working chamber through the outlet.

7. The disinfected environment maintaining system according to claim 6, further comprising a supply device which supplies gas into the working chamber.

8. The sterilizing component removal device according to claim 1, wherein the sprayer sprays, in the working chamber, the liquid in the atomized manner, at a different time from a time when the sterilizing component is sprayed in the working chamber.

9. The sterilizing component removal device according to claim 1, wherein the sterilizing component and the liquid are delivered to the sprayer separately from one another.

10. The sterilizing component removal device according to claim 1, wherein the sprayer further comprises a first sprayer and a second sprayer.

11. The sterilizing component removal device according to claim 10, wherein the sterilizing component is supplied to the first sprayer, and the liquid is supplied to the second sprayer.

* * * * *